(12) United States Patent
Engl et al.

(10) Patent No.: US 8,335,671 B2
(45) Date of Patent: Dec. 18, 2012

(54) MATHEMATICAL DESIGN OF ION CHANNEL SELECTIVITY VIA INVERSE PROBLEM TECHNOLOGY

(76) Inventors: Heinz W. Engl, Linz (AT); Martin Burger, Gallneukirchen (AT); Robert Shim Eisenberg, River Forest, IL (US)

( * ) Notice: Subject to any disclaimer, the term of this patent is extended or adjusted under 35 U.S.C. 154(b) by 756 days.

(21) Appl. No.: 12/297,179

(22) PCT Filed: Apr. 11, 2007

(86) PCT No.: PCT/US2007/008976
§ 371 (c)(1),
(2), (4) Date: Mar. 16, 2009

(87) PCT Pub. No.: WO2007/120728
PCT Pub. Date: Oct. 25, 2007

(65) Prior Publication Data
US 2009/0253898 A1 Oct. 8, 2009

Related U.S. Application Data

(60) Provisional application No. 60/791,185, filed on Apr. 11, 2006.

(51) Int. Cl.
*G06F 17/10* (2006.01)
(52) U.S. Cl. .......................................................... 703/2
(58) Field of Classification Search ..................... 703/2
See application file for complete search history.

*Primary Examiner* — Jerry Lin
(74) *Attorney, Agent, or Firm* — Husch Blackwell LLP

(57) ABSTRACT

Determining the structure of permanent charge for an ion channel formulates an abstract operator, describing ion channel parameters, comprising equations that are ill-posed. The model of ion channel behavior relates the function of the ion channel to the structure of permanent charge within the ion channel and concentrations ions around the ion channel under certain properties and boundary conditions. The model also includes regularization of the abstract operator by approximating the ill-posed equations with a family of well-posed equations. An estimate of the closeness of the well-posed solution to the ill-posed solution is provided. Providing stable and convergent algorithms allows the model to determine a stability for the regularized solution, so that a regularization parameter can determine a balance between the stability and accuracy of the solution.

5 Claims, 15 Drawing Sheets

MATHEMATICAL DESIGN OF ION CHANNEL SELECTIVITY VIA INVERSE PROBLEM TECHNOLOGY

CROSS-REFERENCE TO RELATED APPLICATIONS

This application is the National Stage of International Application No. PCT/US07/08976, filed on Mar. 21, 2002, which, like this application, claims the benefit of U.S. Provisional Application No. 60/791,185. Both references are incorporated by reference as if set forth fully herein.

BACKGROUND OF THE INVENTION

1. Field of the Invention

The present invention relates to methods for characterizing existing ion channels, and designing ion channels with greater specificity for predetermined ions.

2. Background Art

Ion channels are proteins that fold to form a hole down their middle. When properly configured and installed in a cell membrane, ion channels control the movement of ions through the cell membrane. An example of this transport would be the passage of $Na^+$, $K^+$, $Ca^{++}$, and $Cl^-$ ions from the blood stream into and out of cells. The movement of ions into and out of a cell is very important for many processes that are critically related to health and disease in living things, including people. Indeed, ion channels control an enormous range of life's functions by controlling the flow of ions and electricity in and out of cells. A sample ion channel, 100, as illustrated in the prior art is provided in FIG. 1. The port exterior to the cell is labeled 102, and the port to the interior of the cell is labeled 104. The locations of the permanent charges that are the principal influences on how the ion channel conducts ions are labeled 106.

Ion channels conduct one type of ions much better than other types of ions, and this preference for conducting one type of ion over other types of ions into or out of a cell is termed "selectivity." The selectivity of ion channels is a crucial, indispensable part of their function.

If ion channels in living things lose their selectivity, activities critical to sustaining life cease. Thus, if the $Ca^{++}$ channels of an animal or human heart were to become nonselective, or become equally selective to $Na^+$ and $Ca^{++}$, the heart could not beat and death would occur in ~3 minutes.

Ion channels, like many other systems in biology are not perfectly formed; that is to say, they have characteristics which if changed could greatly increase their function. This characteristic of ion channels is particularly clear in the heart. A particular instance of this, the relevance of ion channels to the hearts of certain mammals is explained.

The heart is a sheet of cardiac muscle that is folded to enclose a ventricle, which is a cavity in the heart that holds the blood to be pumped. The ventricle has valves that operate to keep the blood flowing in one direction. The heart works by squeezing the blood out of the ventricle, say the left ventricle. The squeeze must start from the bottom of the ventricle (furthest away from the exit valve and exit artery called the aorta). If the squeeze starts anywhere else, contraction of the heart muscle will be futile, the ventricle will not function as a pump, and the animal or human will will quickly lose consciousness and die. So coordination of the contraction of cardiac muscle is crucial for survival.

In engineered systems of this sort, such as artificial hearts, and in the hearts of lower forms of life, coordination of this sort is done by a control system that is separate from the contractile system. Thus, most invertebrates with hearts control the heart beat with separate nervous systems, and are referred to as having neurogenic hearts. Vertebrates and humans have what are called myogenic hearts, and do not separate the control system from the heart muscle itself. Myogenic hearts use the electrical signal in the contractile tissue itself (the heart muscle) to coordinate contraction. This makes the system very labile and easy to interrupt because any difficulty the tissue has because of its contractile function immediately affects the coordination of the contraction that allows the ventricle to pump blood. Here is where channels come in. If the calcium channels responsible for (a main part of) the coordination of the heart beat are at all disrupted, the heart no longer pumps blood and the animal or person dies. If the calcium flowing through a calcium channel could be increased, the heart would be much less sensitive to this kind of disruption. Thus limitations on the current flow through a calcium channel of the heart is one example of a technical deficiency of the heart. This is just one example. There are many others which physicians and pharmacologists discover every day, unfortunately.

The structures of ion channels are currently identified using X-ray crystallography to measure the positions of the key elements of the protein. Crystallography techniques have several shortcomings, not all of which are listed here. First, the crystallography is time consuming because it takes a long time to obtain a crystal suitable for crystallographic study. Indeed, growing crystals is an art unto itself and most of the proteins of interest in membranes have not been crystallized. Second, proteins can fold differently in different environments. Therefore, even if the ion channel is crystallized, the protein as crystallized may not be in the same environment or state as it is in the animal as it functions. Thus, the crystal structure of the ion channel may not reflect the structure in the form in which it actually functions. Third, the x-ray crystallography studies are only as good as the crystals provided, and take considerable time and resources. Whether the crystal was good enough to obtain the results desired is often not known until after the study is conducted. Fourth, the expertise needed to conduct the x-ray crystallography studies is sufficiently different from the manufacture and design of the channels that it is rare for the same worker to be able to have the complete skill set, and thus workers in the field are dependent on the technical skills of a crystallographer.

The manufacture of ion channels is now sufficiently understood such that if channels can be designed to specification they can be built using the well developed techniques of molecular engineering, e.g., by site directed mutagenesis. One example is given in U.S. Pat. No. 6,979,724 to to Lerman et al. which relates to calcium channel compositions and methods of making and using them. In particular, the Lerman disclosure relates to calcium channel alpha2delta (α2δ) subunits and nucleic acid sequences encoding them. A review of ion channel manufacturing techniques is provided by [130], which should be available to the general public shortly. However, there are present shortcomings in the ability to understand how the structure of an ion channel dictates its function such that the technical ability to make an ion channel is not sufficient to solve problems in the field.

The technical limitations of present design methods are simple to state but hard to remedy. Generally, existing design methods rely on exhaustive trial and error experimentation of the highest quality, energy, and imagination to check reasonable guesses. This approach to design is inefficient and rarely works in complex systems.

There are literally thousands of laboratories doing experiments on ion channels every day all over the world. Almost all of this work is done without theoretical guidance, or rationale, using the trial and error methods of exploration and discovery of traditional biology. Such trial and error methods are essential for learning "the lay of the land", for describing the systems and their components, but they are very inefficient for design. If it was possible to replace trial and error methods with any systematic design tool, the efficiency of thousands of laboratories would be dramatically increased, from nearly zero (which is the efficiency when design is unsuccessful) to a reasonable number.

More recent attempts at design have used simulations of atomic motions, calculations of the movement of every atom of a protein. Such calculations, despite heroic efforts and enormous computers, are unlikely to succeed because biological function occurs on millisecond time scales or slower, and atomic motions occur on 0.0000000000000005 sec time scales (femto seconds and faster). Biological function occurs (in many cases, e.g., in the channels of the heart) only when certain chemicals are present in definite concentrations. Some of these chemicals must be present in micromolar concentration. Thus, atomic scale simulations of these chemicals must include enormous numbers of atoms for many seconds, with motions on the time scale of a femtosecond being resolved. Thus, at this time, atomic scale simulations serve as metaphors and inspiration for design, but not as specific quantitative design methods. While there have been some attempts to use reduced models of channel function that do not include all atomic motions, they have not succeeded in designing a channel of a desired selectivity or in discovering the structure of an ion channel from data taken from the operation of a channel in vivo or in vitro.

Presently, the design theory of ion channels generally analyzes ion channels by linking a model for the electric field in and near the ion channel with a model for ion transport in and near the channel. Generally, such studies are currently conducted using what are termed "one dimensional models," which model an ion channel as a line with charges placed along it in fixed locations. These placed charges are often referred to as "fixed charge" or "stationary charge" to distinguish these charges from the charges of the ions that are moving around and through the channel. The most commonly used models for the ion transport in the vicinity of the channel are built from either the Poisson-Boltzman equations or the Poisson-Nernst-Planck (PNP) equations. Other models used include, but are not limited to, simulations of Brownian motion, simulations of Brownian motion with Poisson equation, and transport Monte Carlo. Viewed in terms of physical chemistry, the models attempt to describe energetics of an ion moving through an ion channel. Viewed mathematically, these equations form what is called a system of non-linear differential equations.

In searching for ion channels with a particular selectivity, different approaches can be taken. One way of solving the selectivity problem would be to hypothesize an ion channel and ask how it might perform for different ions. Efforts to design ion channels by solving ensembles of possible ion channels in the hope of finding suitable structures have not been productive, as illustrated by references [93]-[128].

The ion channel scientists have yet to predetermine a particular selectivity for an ion channel, and then successfully attempt to determine what a channel that would have that selectivity would look like. Many kinds of scientists understand that problems can often be viewed or approached in more than one way depending on the type of information that is available and the type of solution that is desired. Thus, mathematicians know that one may know a cause or stimulus and wish to predict what will happen, or one may be observing effects and wish to infer the cause.

When searching for causes of observed or desired effects the problems are termed "inverse problems" which are likely to be difficult to solve. Two problems are called inverse to each other if the formulation of one problem involves the solution of the other one. These two problems then are separated into a direct problem and an inverse problem. At first sight, it might seem arbitrary which of these problems is called the direct and which one the inverse problem but this arbitrariness is more apparent than real. The problems have quite distinct properties and can be distinguished based on those properties.

Usually, the direct problem is the more "classical" one, in that it usually has a single, obtainable solution, which is termed "well-posed." According to Hadamard, a mathematical problem is called well-posed if for all admissible data, a solution exists, for all admissible data, the solution is unique, and the solution depends continuously on the data.

Much of the mathematical theory of partial differential equation deals with the question what "admissible data" means and in which sense "solution" is to be understood for specific classes of partial differential equations.

The direct problem usually is to predict the evolution of the studied system (described e.g. by a partial differential equation) from knowledge of its present state and the governing physical laws including information on all physically relevant parameters including boundary conditions and initial conditions. Boundary conditions are parameters that describe the behavior of the physical system or set of equations at the edges of a simulation region. Conditions imposed at the starting time for a problem where the conditions change over time are called initial conditions.

Those of ordinary skill in the art will appreciate that boundary conditions and initial conditions are much more important than they may seem at first to the uninitiated. Boundary conditions and initial conditions describe what is put into the system and what comes out of it. They describe the flow of energy, matter, electric charge, et cetera that are forced to enter and leave the system. Boundary conditions are fully as important as the system itself in determining the overall properties of a practical system. Indeed, there are many engineering systems that are designed to have specific inputs and outputs (i.e., initial and boundary conditions) only. That is to say, there are many engineering systems designed so the user does not need to be concerned what is inside the "black box" (i.e., inside the system) but only needs to be concerned with the inputs and outputs (i.e., boundary and initial conditions). Thus, in electronics, a well designed amplifier has a simple relation between input and output (called gain) and the user does not have to worry if the amplifier uses field effect transistors, bipolar transistors, or even old fashioned tubes to make that gain.

If the number and type of boundary/initial conditions is correct and the parameters are sufficiently smooth, then the direct problem is almost always well-posed and therefore easier to solve than the related inverse problem. Indeed, if the problem is not amenable to classical methods of solution (when given correct boundary/initial conditions, and reasonably smooth parameters), most scientists would conclude the theory and problem were mistaken and should be abandoned. Thus, it is characteristic of established models that their forward problems are well posed.

There are also intrinsic mathematical properties that permit one to decide which of the problems is called the "inverse" one, namely the fact that the inverse problem is usually "ill-posed."

If one of Hadamard's conditions for terming a problem well-posed is violated, then the problem is called ill-posed. For an ill-posed problem neither the existence nor the uniqueness of a solution to an inverse problem is guaranteed. A unique solution necessarily denies the problem solver the ability to select which properties to favor in a solution. There is only one solution! However, ill-posed problems may lack any solution, or solutions may exist but are not unique (which is to say there may be more than one answer), and/or (unique or non-unique) solutions are not stable with respect to noise, modeling errors or other, even numerical, inaccuracies.

The process of bringing stability back to these problems is termed regularization. Often, regularization is done by imbedding an ill-posed problem into a collection of well-posed problems depending on some parameter, where the original ill-posed problem is a limiting case of this family of well-posed problems with respect to this parameter.

Non-uniqueness is sometimes an advantage, because non-uniqueness can allow a choice among several strategies all of which achieve a desired effect. The non-uniqueness of the solution can be advantageous because one strategy might have better properties than another. When solving design problems there is a substantial value to having a choice of solutions because that allows the problem solver to choose from different possible designs based on practical advantages not included in the mathematical model itself. This is in contrast to an identification problem where having a choice of solutions means that the identification is ambiguous.

In the case of designing ion channels it is advantageous to look for values of parameters (possibly fulfilling additional constraints) that achieve certain design goals (like selectivity in ion channel design). In contrast, in an identification problem, one wants to infer ('identify') values of parameters from indirect measurements, i.e., parameters are estimated not from direct measurements of the parameters but from measurements of other quantities from which estimates of the parameters are made. These other quantities appear in the mathematics as quantities in the output of the forward problem (and its boundary conditions). The inverse problem is used to estimate these parameters from measurements of the output under some conditions or other, or from multiple measurements of the output under a set of conditions (to give more information and reduce sensitivity to, for example, mistakes and noise). Here, in solving this inverse problem, uniqueness ("identifiability") is of great importance.

Uniqueness questions are dealt with explicitly in one part of the mathematical literature of inverse problems, but as soon as one wants to compute solutions of inverse problems, one almost always has to deal with the issue of (in)stability: In practical applications, one never has exact data, but only data perturbed by noise produced by systematic or statistical errors in the measurements or produced by errors in the mathematical model itself. Models are often only a representation of reality with limited accuracy. Even if the random and/or systematic deviation from the data is small, or the error in the model is small, algorithms developed for well-posed problems will fail if they do not address the instability in the overall process of estimation of parameters. If they do not address the instability of the inverse problem due to a violation of the third Hadamard condition, data as well as round-off errors can then be amplified by an arbitrarily large factor (depending on error characteristics) arising from this lack of continuous dependence, the violation of the third Hadamard condition. This is the main effect of the lack of continuous dependence. One can quantify this effect, thus classifying ill-posed problems roughly into mildly and severely ill-posed problems depending on how strong the error amplification is. This classification has to do with the rate at which the spectrum (for a linear problem, or for the linearization of a non-linear problem) tends to 0, see, e.g., [23].

Important and well studied classes of inverse problems which provide technical solutions to technical problems are, e.g.

(Computerized) tomography (cf. [56]), which involves the reconstruction of a function, usually a density distribution, from values of its line integrals and is important both in medical applications and in nondestructive testing [28]. Mathematically, this is connected with the inversion of the Radon transform.

Inverse scattering (cf. [17], [65]), where one wants to reconstruct an obstacle or an inhomogeneity from waves scattered by those. This is a special case of shape reconstruction and closely connected to shape optimization [41]: while in the latter, one wants to construct a shape such that some outcome is optimized, i.e., one wants to reach a desired effect, in the former, one wants to determine a shape from measurements, i.e., one is looking for the cause for an observed effect. Here, uniqueness is a basic question, since one wants to know if the shape (or anything else in some other kind of inverse problem) can be determined uniquely from the data ("identifiability"), while in a (shape) optimization problem, it might even be advantageous if one has several possibilities to reach the desired aim, so that one does not care about uniqueness there.

Inverse heat conduction problems like solving a heat equation backwards in time or "sideways" (i.e., with Cauchy data on a part of the boundary) (cf. [30]).

Geophysical inverse problems like determining a spatially varying density distribution in the earth from gravity measurements (cf. [27]).

Inverse problems in imaging like deblurring and denoising (cf. [14, 55, 60])

Identification of parameters in (partial) differential equations from interior or boundary measurements of the solution (cf. [3], [46]), the latter case appearing e.g., in impedance tomography (cf. [45]). If the parameter is piecewise constant and one is mainly interested in the location where it jumps, this can also be interpreted as a shape reconstruction problem.

Some common features of inverse problems that provide technical solutions to technical problems are problems such as amplification of high-frequency errors, a need to use one or both of a priori information and regularization to restore stability, errors of differing natures that require separate treatment, and intrinsic information loss even if one does everything in the mathematically best way. Examples of errors requiring different treatment are errors of approximation, which are how closely the model is hewing to the actual system, and the propagation of data error, wherein errors in earlier calculations cause greater errors in later calculations.

Detailed references for these and many more classes of inverse problems can be found e.g., in [23], [20], [22], [37], [53], [50], [44], [16]. In order to overcome these instabilities and design solution techniques for inverse problems which are robust (i.e., stable with respect to data and numerical errors), one has to design and use regularization methods, which in general terms replace an ill-posed problem by a family of neighboring well-posed problems.

It would be desirable to be able to control the structure and selectivity of ion channels, and even more desirable to be able to reliably design ion channels with specifically predetermined selectivity. More desirably, such methods would not use trial and error approaches that require solving ensembles of possible ion channels in the hope of fortuitously finding the desired result. This would be especially advantageous where existing ion channels are less than optimal for the function that they perform. This would be of greatest importance if the technology were able to characterize and design the selectivity of ion channel functions that are important to the life and health of animals, including humans.

Further, if the methods could pioneer the identification and design of selectivity through in vitro and in vivo experiments, the technical horizons of laboratory work in the field would be significantly broadened accelerating not only design, but also manufacture and testing. Similarly, if the technology that solved the problems of the identification of structure and design of selectivity could be applied to a broad range of models, the ability of theoretical workers to contribute to the solution of existing technical shortcomings of existing ion channels would be similarly amplified.

BRIEF SUMMARY OF THE INVENTION

A model for determining a structure of permanent charge for an ion channel from information formulates an abstract operator describing ion channel parameters comprising equations that are ill-posed for determining the structure of permanent charge of an ion channel. The model of ion channel behavior relates the function of the ion channel to the structure of permanent charge within the ion channel and the concentrations of ion species present in the region in and adjacent to the ion channel given that certain properties and boundary conditions are known. The model also includes the regularization of the abstract operator by approximating the equations that are ill-posed for determining the structure of permanent charge of an ion channel with a family of well-posed equations to provide a regularized solution of ion channel parameters. An estimate of the closeness of the regularized solution to the solution is provided via the abstract operator to obtain an accuracy of the regularized solution. Providing stable and convergent algorithms allows the model to determine a stability for the regularized solution, so that when at least one regularization parameter is provided, the regularization parameter can determine a balance between the stability stability of the regularized solution and the accuracy of the regularized solution.

In one embodiment of the invention, formulating the abstract operator includes providing a forward model of ion channel behavior, information regarding the structure of permanent charge for a control ion channel, and a plurality of sets of mobile species concentration information, where a set of mobile species concentration information comprising a concentration of the first mobile species and a concentration of the second mobile species. Then, a corresponding ensemble of data for the relationship of current to voltage for the control ion channel can be provided for each of the plurality of sets of mobile species concentration information. The forward model of ion channel behavior can then be solved for the control ion channel based on the mobile species concentrations and the relationship of current to voltage.

In another embodiment of the invention, the forward model of ion channel behavior for the control ion channel further can be solved by providing a fast and accurate algorithm for the forward mode, and providing an accuracy for the forward model.

In another aspect of the invention, a structure of permanent charge of an ion channel can be determined from indirect data comprising mobile species concentration data, applied voltage data, and current-voltage relationship data. If a model for determining the structure of permanent charge as previously mentioned is provided, then control data comprising control permanent charge data, control mobile species data, control applied voltage data, and control current-voltage relationship data can also be provided. This allows the model for determining the structure of permanent charge to be applied to the control data.

In an exemplary embodiment of the present invention, the ion channel model is a Poisson-Planck-Nernst model. In another exemplary model of the present invention, regularizing the abstract operator uses regularization methods from the group consisting of variational and iterative approaches. One application of the invention is to design a structure that includes a selectivity of the ion channel between at least a first mobile ion and a second mobile ion, and the structure is determined from the selectivity. Optionally, a structure is identified based on indirect data that is experimental data derived from measuring an actual ion channel. Alternatively, an ion channel can be constructed according to a design created by the methods described.

The invention further contemplates using an ion channel according to the disclosed methods, such that the ion channel has a first opening and a second opening, and the ion channel is installed in a membrane, such that if the membrane has a predetermined electrical potential across the membrane, the ion channel will select, relatively, for the transport of the first mobile ion species relative to the transport of the second mobile ion species.

In another aspect of the present invention, the model for determining the structure of permanent charge includes determining the manufacturability of a the determined structure of permanent charge for the ion channel from the structure of a pre-existing ion channel. This can be done by providing the structure of a pre-existing ion channel; and applying the model to the structure of the pre-existing ion channel. This alternatively includes constructing an ion channel for a predetermined function by designing an ion channel suitable for carrying out the predetermined function using the methods described, and constructing an ion channel that approximately embodies the ion channel designed for carrying out the predetermined function.

One benefit of the present invention is that workers in the field will be able to control the structure and selectivity of ion channels, and be able to reliably design ion channels with specifically predetermined selectivity. More beneficially, such methods would not use approaches that require solving ensembles of possible ion channels in the hope of fortuitously finding the desired result. The invention is especially advantageous where existing ion channels are less than optimal for the function that they perform. This would be of greatest benefit in areas where the ability to characterize and design the selectivity of ion channel functions that are important to the life and health of animals, including humans.

Scientific benefits are also available. The methods permit identification and design of selectivity through in vitro and in vivo experiments, accelerating the technical horizons of laboratory work in the field, as well as manufacture and testing. Because the present technology can be applied to a broad range of models, the ability of theoretical workers to contribute to the solution of existing technical shortcomings of existing ion channels will also be similarly amplified.

Still further benefits and advantages of the invention will be apparent to the skilled worker from the discussion that follows.

BRIEF DESCRIPTION OF THE SEVERAL VIEWS OF THE DRAWING(S)

DETAILED DESCRIPTION OF THE INVENTION

1. Introduction

For the purposes of the present disclosure, solving the forward problem derives a current-voltage relationship from a predetermined structure of permanent charge (synonymous with "fixed charge") and predetermined concentrations of mobile species, and the electrical potential (sometimes referred to as "voltage") across the ion channel.

The forward problem of calculating the voltage-current-curve from the permanent charge can be reversed to present two similar, but distinct, inverse problems. The first inverse problem is the identification of the structure of permanent charge in an ion channel. The second inverse problem is the design of the structure of permanent charge for an ion channel. While the mathematical problems presented in solving the identification and design problems are different, these problems relate to each other because they are directed to the same model system, the model established by the forward problem.

Figure 2:
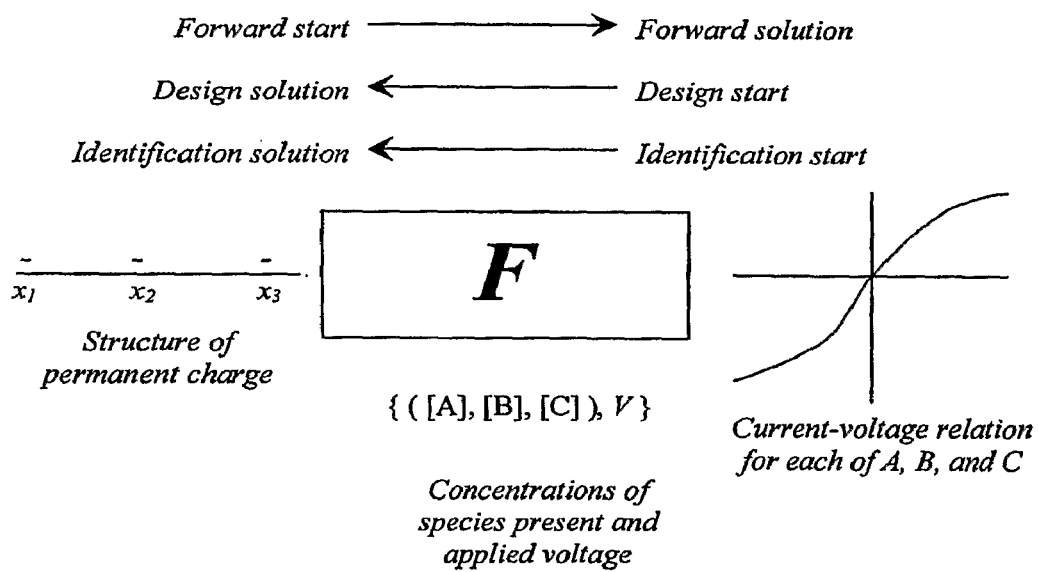
FIG. 2 is a diagram illustrating how the function F relates the structure of permanent charge, the concentrations of the mobile species and the current-voltage relationship.

Referring to FIG. 2, a cartoon illustrates the distinctions between the forward problem and the inverse problems. The structure of permanent charge, 202, illustrated by a line with charges distributed along an x-axis, defines the locations of charge in a one-dimensional space. The concentrations of mobile species, 204, define the concentrations of different mobile species to be modeled, and constitute inputs to both the forward and inverse problems, along with V, applied voltage. Generally, this will include the solvent, the ions to be selected for and against, and counterions for the ions that are subject to selection or non-selection. The current-voltage relationship, 206, describes the line, or set, of relationships that describe how many ions move through the channel at a particular voltage. It should be noted that for each structure of permanent charge, there are infinite ensembles of relationships between the ion concentration and applied voltage inputs and the voltage-current relationships.

The structure of permanent charge, 202, is the electrical structure of the system. Like any structure it provides the framework for what a system can do but it does not tell what the system does until driving forces and control signals are applied to the system. Think of a car. The structure of the car tells a lot about the car and knowledge of the structure is necessary to understand and improve the car. But the car does not move unless gasoline is in the tank, water in the radiator, lubricants and oils in the right places (etc), and the car does not move until a control signal is given telling it to move. The automobile needs driving forces (the gasoline), supporting items (water and oil), and a control signal too. Ion channels are similar. They need driving forces. The driving forces for ion flow through channels are the concentrations of ions outside the channel and the electrical voltage across the channel. The supporting forces are the dielectric properties of the lipid membrane and various biochemicals. The control signal is different for different types of channels. In some it is a specific chemical; in others it is pressure; in others the control signal is voltage. Thus, we see that the properties of any channel structure correspond to a multitude of ensembles of properties of current voltage curves. Each different driving force gives a different current voltage curve. Each different biochemical or dielectric property gives a different current voltage curve. Each chemical or pressure gives a different current voltage curve. And each driving force at each pressure gives a different current voltage curve. Thus, the number of current voltage curves is as large and disparate as the number of trips a car can take. The car has only one structure but it can go many places in many different ways.

It is often useful to solve a problem such as illustrated in FIG. 2 for a variety of different concentrations of mobile species and voltages, which can be referred to as an ensemble (or set) of conditions. In solving the classical version of the ion channel system (or "forward problem" in the mathematical language), physical chemists typically calculate a current voltage relationship (or "curve"). These curves rectify (i.e., they are not straight lines) but they do not oscillate wildly.

Thus, each current voltage curve can be described adequately by a complicated polynomial equation with 5 parameters or thereabouts. The current voltage curves are generally studied from the smallest detectable currents, say 0.1 pA, to the largest allowable applied voltage which is typically 150 mV. No time dependence is involved when only open channels are studied. Open channel currents are independent of time from approximately 1 μsec to the longest times that can be studied, e.g., seconds. Current voltage curves vary depending on the ions present to carry current. Thus current voltage curves are typically measured first in a "pure" systems consisting of one electrolyte (like NaCl) on one side of the channel and the same electrolyte on the other side of the channel. Measurements are then made for a series of different concentrations. First, the concentrations are the same on both sides, so typically measurements would be made at 20 mM, 50 mM, 100 mM, 500 mM, 1 M, 2 M NaCl. Then different concentrations would be used on the two sides, with all combinations being explored, e.g., 20 mM on one side with 50 mM, 100 mM, 500 mM, 1 M, 2 M NaCl on the other. Lower concentrations than 20 mM would be avoided because they tend to damage the channel protein. Then the ion would be changed. Typically, $Li^+$, $Na^+$, $K^+$, $Rb^+$, and $Cs^+$ would be studied. Then mixtures of ions would be studied, starting with two at a time, e.g., NaCl and KCl mixtures on both sides of the channel but at different concentrations (in most cases). Work would then be done on divalent ions. Here concentrations would often be much lower because biological channels work better in low divalent concentrations. Typical ions would be $Ca^{++}$ and $Ba^{++}$ but others are often used as well. Current can be carried by hydrogen ions and hydronium ions so pH is often varied as well. Finally, 'exotic' organic cations like choline or tetramethylammonium are often used as well as less exotic organic anions like amino acids.

Figure 3:
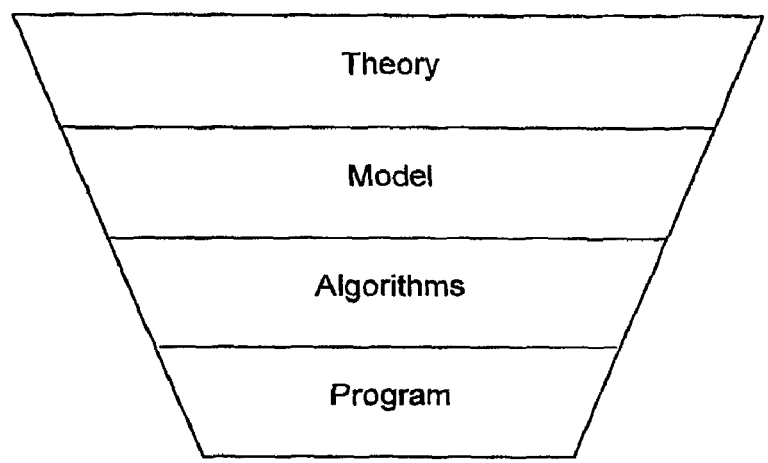
FIG. 3 is a diagram illustrating how theory, models, algorithms, and the computer program are related to each other.

In the middle of FIG. 2 is a box that represents the physics that relates the structure of permanent charge, mobile species and applied voltage inputs, and the current-voltage-relationship to each other. In describing the physics of ion channels, how the structure of permanent charge of an ion channel relates to the current-voltage relationship as a function of mobile species concentrations and for the purposes of the present discussion is embodied in a function F, which, in an abstract sense, symbolizes how structure is transformed into the observable or desired output. Referring to FIG. 3, F can be described on a variety of levels, with a variety of resolutions. At the highest level is the theoretical physics or chemistry selected for describing the interactions of the parts. However, in order to solve the problem a more concrete level of description is needed that necessarily imposes some degree of approximation in order to create a model to describe F. A model is a set of equations that are selected to concretely describe the interactions indicated by the theoretical physics and chemistry. Before the model can be implemented computationally, a set of algorithms is selected in order to make a solution computable, and preferably, efficiently computable. Making the solution computable or efficiently computable will usually require yet another level of approximation. Last, the model as implemented with the selected algorithms is embodied in computer code so that a result can be obtained from a computer having a processor to execute the calculations and a memory to store inputs and outputs for the processor. The result may be used in any way that is common for computer implemented solutions, for example by displaying the result (such as on a monitor or projector), saving the result (into non-volatile memory, such as hard disks or flash memory), transmitting the result to another program to conduct further calculations (via local area networks, wide area networks, or modem, serial or other connection). The choice and design of algorithms may involve approximations so the problem will fit in the available memory and run with reasonable speed on the processors available. Each aspect of this invention should be understood to be operable at all of these levels, from the most abstract to the useful, tangible and concrete results.

Mathematically, the present approach for identifying and designing ion channels formulates the inverse solution of permanent charge as an abstract operator equation or optimization problem involving models for the flow of electrical charge through the channel. The abstract operator equation is ill-posed and can be regularized (used in the most general sense) using several methods, exemplarily in this disclosure by using iterative methods with appropriate stopping criterion. Alternatively, or in addition, the abstract operator equation can be regularized by using an additional penalization of the objective functional in the formulation as optimization problem, in order to be able to solve the problem numerically in an efficient, stable and robust way. Because the inverse problems are ill-posed in the sense that small differences in the electrical current can correspond to large differences in the permanent charge, regularization is necessary. In the context of identification, the regularization methods are desirable to allow one to compute a stable approximation of the real permanent charge in the channel. In the context of design, regularization methods are desirable so one can introduce a-priori ideas of suitable designs, such as attempting to conform suitable designs to being easily engineered variations of existing designs.

This disclosure describes, among other things, how to perform ion channel design and identification. First, a class of models is used that is believed to reasonably describe the function of ion channels if all of the parameters and boundary conditions are known. Second, a class of algorithms that can be used to efficiently and stably solve the related "inverse problem" is described. Finally, the disclosure shows by examples that these methods succeed in both the tasks of identification and design. While the steps of solving the problem are described from beginning to end, those of ordinary skill in the art will appreciate that each of the steps influences the others, and that the solution to this class of problems, and the example in particular, may be performed partly or wholly out of the listed order. As will be appreciated by those of ordinary skill in the art, or have studied the field of applied mathematics, much of the education of an advanced undergraduate or graduate student in applied mathematics is devoted to teaching how the steps influence each other, and how to vary the order of the particular steps of the solution.

The first class of models that describe the function of ion channels is termed here the "direct problem" or "forward problem." This includes selecting interactions to describe the physical system, mathematically describing those interactions in a model or models, selecting computational schemes or algorithms to implement the models, and then programming the necessary computer code, with its attendant limitations, to reach a result.

2. Modeling Ion Channels

Models for ion transport through channels presently incorporate the following effects:

Electrostatic interaction between the charged particles, whether mobile or permanent Generation of net charge by the mobile ions and a consequent change of the electric field and electrical potential Generation of ion flux by the electric field and concentration gradient Direct electro-chemical interactions between the ions; for example, interactions caused by the finite diameter of ions.

Figure 1:
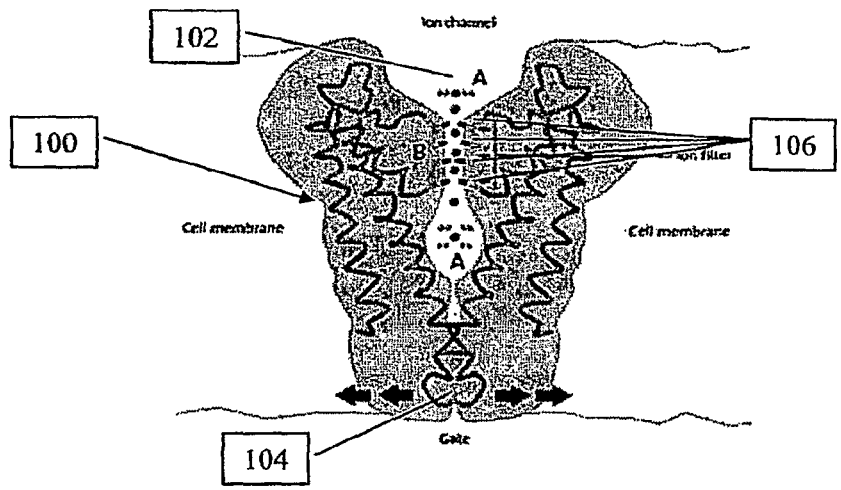
FIG. 1 is a cartoon depicting a cross-section of an ion channel.

The exemplary embodiment is described as a "one-dimensional" model. Therefore, referring to FIG. 2, permanent charges are described in terms of an amount of charge placed along a line. Referring to FIG. 1, from URL:fig.cox.miami.edu/~cmallery/150/memb/ion_channels.htm, if one visualizes an ion channel as a tube, then, the structure of permanent charge can be understood as locating charge along the line in the center of the tube. The one dimensional solution tells one how far into the tube the charges are, but not how far away from the center line or at what angle the charge is located at. This one-dimensional model of a three-dimensional ion channel is an approximation that reduces the computational complexity and hence computation time for solving the model. However, at the expense of significantly complicating the computations, the one-dimensional model can be replaced by those of ordinary skill in the art with two-dimensional or three-dimensional models, and the present invention is not limited to one-dimensional models, or even any particular one-dimensional model. Indeed, students and postdoctoral fellows in molecular biophysics and computational biology learn to switch between one, two and three dimensional models to choose what is needed to solve the particular problem at hand with available computational resources.

Further, in the exemplary embodiments, models for various physical aspects of the systems such as electric field or ion transport are used. The models selected are believed to be the best approach to solving problems of this sort at this time, but other models could be used to model the various physical behaviors in this invention. Accordingly, the present invention should not be considered to be limited to particular models for the systems analyzed.

Turning to the definition of the class of models that are the forward problem, a first model is selected to describe the electric field, and a second model is selected to describe the diffusion of ions in the region of the ion channel. These two models interact with each other. In the exemplary embodiment of the present invention the model for the electric field is a Poisson equation with a source term equal to the charge generated by the ions. Also in the present exemplary embodiment, differential equations are usually used to describe the continuum description of ion transport, in particular the so-called Nernst-Planck (NP) equations, which are an application of the usual laws of diffusion ('Fick's laws') to charged particles like ions. The solutions of the Nernst-Planck equations are the number densities of ions expressed as functions of their spatial location, in the channel and surrounding baths. The Nernst-Planck equations can involve a diffusion term, a drift term caused by the electric field (ideal electrostatic potential), by an external constraining potential, and by the excess electro-chemical potential. Alternative models for the electric field could be Coulomb's law applied to all charges in the system, Coulomb's law applied to periodic boundary conditions, Coulomb's law with Ewald sums applied to periodic boundary conditions, Particle-Particle-Particle Mesh, Particle-Particle-Particle Mesh with double counting corrections. Alternative models for the description of ion transport could be Brownian dynamics, Langevin dynamics, molecular dynamics, Transport Monte Carlo, and barrier models.

When the Poisson equation and the Nernst-Planck equations are used together to create a model, the coupled system for electric field and ion densities is then commonly called a Poisson-Nernst-Planck (PNP) model. At equilibrium, the solution of the model can be characterized as the minimum of an energy minimization problem. However, in most practically relevant situations—with an applied voltage and a control of the ion densities in the bath—the system is perturbed from from equilibrium. Alternative model systems to the PNP models are: CPNP, i.e., correlated PNP; improved PNP, Brownian dynamics, Langevin dynamics, molecular dynamics, Transport Monte Carlo, and barrier models all with Poisson. While not all alternative model systems may be amenable to the particular methods exemplified in this disclosure, those of ordinary skill in the art of solving non-linear differential equations can identify methods appropriate to those models. Much of training students and postdoctoral fellows in the art of solving nonlinear differential equations is devoted to learning how to apply well established methods to different models.

The PNP model can be set forth as follows. Though there are many known variations of the PNP modeling approach, the present invention is not limited to a particular model of the interactions. In a computational domain $\Omega$ modeling the bath and ion channel region, the general structure of the model for describing the unconstrained electrical behavior of the mobile species of interest is of the form of the linked equations:

$$-\lambda^2 \Delta V = \sum_k z_k \rho_k \quad (1)$$

$$-\nabla \cdot (\rho_j \nabla \mu_j [\rho_1, \ldots, \rho_M, V]) = 0 \quad (2)$$

where $V$ is the electric potential, $\rho_k$ denotes the density of mobile species k with charge $z_k$ and mobility $m_k$. $\lambda$ is a dimensionless parameter whose size is inversely proportional to the scaling of the permanent charge in the channel. In particular, for a large permanent charge relative to the scaling to the system size one can expect $\lambda$ to be small, and hence equation (1) becomes a singularly perturbed Poisson equation, which creates various mathematical and computational complications. The complications include, but are not limited to different forms of the solution, multiple values of the solution, computational difficulties arising from the singular or nearly singular form of the problem, and other problems characteristic of singularly perturbed systems of partial differential equations as will be well known to those of ordinary skill in the art of solving singularly perturbed non-linear differential equations.

The potential $\mu_k$ is the functional variation of energy functional E with respect to the density $\rho_k$ i.e., $$\mu_k = \frac{\partial}{\partial \rho_k} E[\rho_1, \ldots, \rho_M, V]. \quad (3)$$

The Poisson equation (1) is an equilibrium condition for the energy functional, i.e., $$0 = \frac{\partial}{\partial V} E[\rho_1, \ldots, \rho_M, V]. \quad (4)$$

As previously mentioned, the total equilibrium is usually perturbed by boundary conditions—otherwise flow and current would be identically zero for all mobile species, including linear combinations of chemical mobile species of like charge—which fact is evident from the Nernst-Planck equation (2), which does not enforce equilibrium of the ions ($\mu_k=0$) in general, but only for special boundary values such that $\mu_k=0$ on $\partial\Omega$. Ion channels do not function at equilibrium and so equilibrium analysis alone is not sufficient.

The energy functional can be written in the form $$E[\rho_1,\ldots,\rho_M,V] = \int_\Omega (-\lambda^2|\nabla V|^2 + z_k V\rho_k + D_k\rho_k \log \rho_k + \mu_k^0 \rho_k)dx + E^{ex}[\rho_1,\ldots,\rho_M] \quad (5)$$

with $D_k$ denoting a diffusion coefficient, $E^{ex}$ denoting the excess electro-chemical energy and $\mu_k^0$ denoting the external constraining potential acting on mobile species k. Those of ordinary skill in the art will appreciate that the energy functional could be written in other forms, and that while the present invention is exemplified by this energy functional, it is not limited to this form of the energy functional. The energy functional is a subject of active investigation in the field of statistical mechanics of simple and complex fluids. Some forms of it are given in the Mean Spherical Approximation and Hypernetted Chain Theories, others in various versions of Rosenfeld's Density Functional theory, including those optimized to include electrical potential, and in the White Bear Functional.

The system defined this way is coupled to a constitutive model showing how the potentials arise from the structure and physics of the channel. Again, while the invention is exemplified by a particular model, it is not limited to the particular model. The excess electrochemical potentials (obtained as variations of the excess free energy with respect to the particle densities) describe the direct interactions between the ions, and are usually obtained from hard-sphere models or Lennard-Jones potentials. The external constraining potential describes the external forces on the ions due to the structure and chemical nature of the channel. The external constraining potential is of particular relevance for the ions creating the permanent charge of the channel because the external constraining potential determines the confinement to the selectivity filter, thereby having a large effect on the selectivity of the channel.

In the exemplary embodiment, a specific model based on density-functional theory (DFT) and mean-spherical approximations (MSA), as described in [34, 35, 59] is used, but as will be appreciated by those of ordinary skill in the art, the treatment of other models for excess electro-chemical potentials can be carried out with similar computational schemes and leads to the same kind of inverse problems as described below. Graduate students and postdoctoral fellows in statistical mechanics of simple and complex fluids are ordinarily trained in the skill of constructing and using similar models.

The standard computational schemes for PNP-systems can be based on an iterative (sequential) decoupling of Poisson and Nernst-Planck equations (Gummel-type methods) or coupled Newton-iterations. See references [77]-[91]. The disadvantage of Gummel-type iterations is a non-robustness with respect to certain parameters in the selected model, in particular V and $\lambda$. Newton-type methods are more robust, but still the (non-symmetric) linearized problem to be solved in each iteration step is not well-posed for large parameters. Moreover, as usual for Newton methods, one needs additional globalization techniques.

The present disclosure presents an approach based on a symmetric linearization of the problem, which is motivated by the energy minimization approach used in equilibrium situations. In the non-equilibrium case some modifications are necessary, but the symmetry of the system can be preserved. Moreover, the form of the energy functional illustrated here permits a so-called mixed finite element approximation, i.e., where the densities are approximated by discontinuous functions (e.g., piecewise continuous ones) across a partition of the domain (into subintervals in one dimension), and the fluxes $J_k = z_k m_k \rho_k \Delta\mu_k$ are approximated by continuous functions (e.g., piecewise linear ones). While those of ordinary skill in the art of solving differential equations are familiar with mixed finite element approximations, those workers from other fields seeking information can find an adequate references in [129].

For the electric potential V a standard finite element discretization with continuous Ansatz functions (e.g., piecewise linear) can be used, because the gradient of V also appears in the energy functional. With this discretization, an iterative scheme is obtained, where a symmetric linear system has to be solved in each step, with the unknowns being the coefficients of the finite element basis functions.

With standard finite element discretization with continuous Anzatz functions and computations of the excess electrochemical potential as in [34], an iterative scheme based on the solution of symmetric linear systems in each iteration step is constructed. The iteration constructs a sequence $(\rho_1^n, \ldots, \rho_M^n, V^n)$ and additionally fluxes $(J_1^n, \ldots, J_M^n)$ by solving coupled linear systems of the form $$\lambda^2 \Delta V^n + \sum_k z_k \rho_k^n = 0 \quad (6)$$

$$\frac{J_j^n}{z_j \rho_j^{n-1}} - \nabla \mu_j^n = 0, \quad (7)$$

$$\eta_n(\rho_j^n - \rho_j^{n-1}) - \nabla \cdot J_j^n \quad (8)$$

or more precisely their mixed finite element discretizations. Here $\eta_n \geq 0$ is a damping parameter that can be adapted to obtain global convergence, and $\mu_j^n$ is a linear approximation of $\mu_j[\rho_1^n,\ldots,\rho_M^n,V^N]$ (linear with respect to the sequence $\rho_1^n,\ldots,\rho_M^n,V^N$]. It turns out that this scheme is not only robust with respect to the major parameters, but even leads to decreasing iteration numbers with decreasing Debye length $\lambda$, which is an important feature since the scaling of most interesting systems yields a small value of this parameter. As disclosed below, the solution of inverse problems will force the forward problem to be solved a very large number of times, so that efficiency in the computational methods for the forward problems is crucial.

Figure 4:
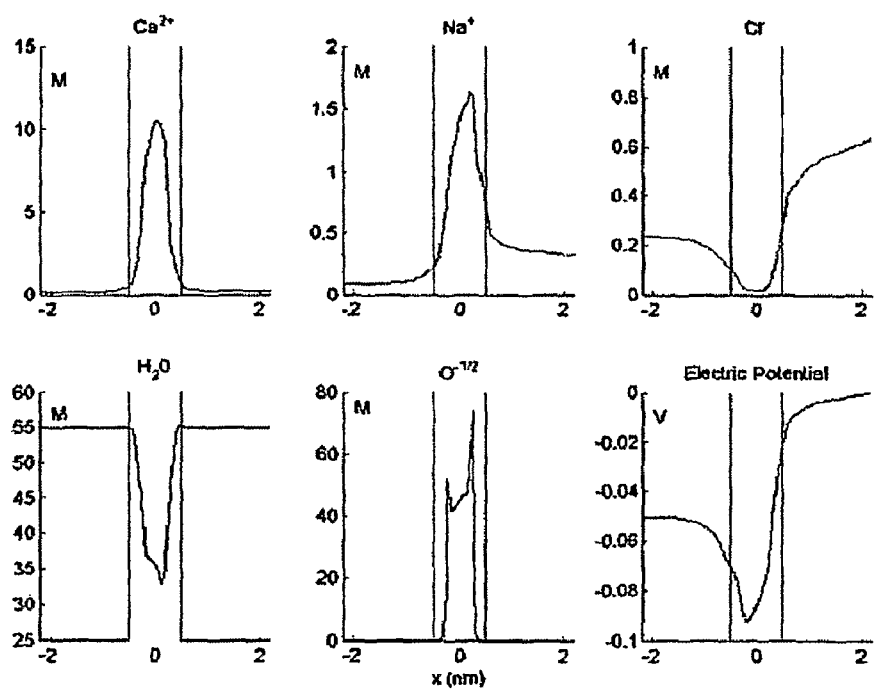
FIG. 4 is a plot of ion densities and electric potential as functions of spatial location, for an L-type Calcium channel with applied voltage 50 mV.

To solve the forward problem, data about a particular ion is needed. The solution of the forward model for an L-type Ca-channel (described in detail in [34]) is illustrated in FIG. 4. The data from [34] is used to provide values for the parameters identified by fixing the locations of the fixed or permanent charges. In this channel, there are three mobile ion species, $Ca^{++}$, $Na^+$, $Cl^-$, a neutral mobile species $H_2O$, and one confined species (the permanent charge species), namely half-charged oxygens $O^{-1/2}$. Half charged oxygens are typically not free oxygen, but instead are portions of functional groups on organic molecules in the protein such as carboxyl groups. $K^+$ could be included, but is left out in this disclosure only to simplify the presentation of the invention. The demarked central regions correspond to the ion channel, the exterior region to the left and right the model bath that corresponds to the contents of the inside or outside of a cell membrane. In this example (with an applied voltage of 50 mV and ion densities controlled in the baths away from the channel region, by either the experimental apparatus or other systems in the biological cell) one observes many typical effects, in particular the selectivity properties of the channel. Due to the negative permanent charge (oxygens $O^{-1/2}$), there is an attractive electrostatic force on the positively charged ions ($Na^+$ and $Ca^{++}$) and a repulsive force on the negatively charged ions ($Cl^-$). Moreover, there are additional chemical forces (important in particular due to the narrow cross section of the channel) which cause an additional decrease of the densities in the channel region. This decrease can be observed in particular in the plot of the water density, since it is the only force acting on this species, there being no net electromagnetic interaction due to overall charge neutrality. The permanent charge of this channel is represented by the half-charged oxygens $O^{-1/2}$, which are confined to the channel. The confinement is caused by the external constraining potential, which is represented by $\mu_k^0$ (with k being the index of the oxygens), the shape of the oxygen density inside the channel is determined by this potential, the total number $N_k=8$ of the $O^{-1/2}$ oxygens, as well as the interactions with the other species. The inverse problems discussed in the following section will deal with the determination of the properties of the permanent charge, i.e., the oxygens in this example:

3. Regularization Methods for Nonlinear Inverse Problems

As those of ordinary skill in the art will appreciate, usually the mathematically most efficient way to formulate inverse problems involving partial differential equations uses concepts and methods from functional analysis. Nonlinear inverse problems can then be cast into the abstract framework of nonlinear operator equations $$F(x)=y, \quad (9)$$

where the operator F acts between two function (e.g., Hilbert) spaces X and Y. The basic assumptions for a reasonable theory are that F is continuous and is weakly sequentially closed, i.e., for any sequence $x_n \subset D(F)$, $x_n \to x$ weakly in X and $F(x_n) \to y$ weakly in Y imply that $x \in D$ and $F(x)=y$. (cf. [23, 24]). As opposed to the linear case, F is usually not explicitly given, but represents the operator describing the direct (also sometimes called "forward") problem. For example, for the ion channel model described previously, F would be the operator F mapping the constraining potential $\mu_j^0$, (with j being the index corresponding to the permanent charge) into the outflow current used later to describe the inverse problem of identifying the constraining potential related to the permanent charge. Thus, computing a value of the operator F for a given input x involves solving the problem (1), (2), which is quite a difficult task. The values of a derivative of F or values of an approximation to the derivative need to be computed, which involves solving a linearized partial differential equation. These computations appear in solution methods for inverse problems several, possibly many, times, so that efficient solution techniques for the direct problem and for its linearizations have to be found and efficiently coupled with solution strategies for the inverse problem.

As a relatively simple example (not related directly to the ion channel problem) to illustrate this point (and also to illustrate a specific algorithm below), we use the following model problem. The problem, in its one-dimensional version described further down, describes the heat and temperature in a bar of material that is kept cold at either end, but may be heated in the middle:

The temperature u (as a function of location after sufficiently long time, i.e., in equilibrium) of a conducting material occupying a three dimensional domain $\Omega$ whose temperature is kept zero at the boundary can be described by $$-\nabla \cdot (q(x)\nabla u)=f(x) \ x \text{ in } \Omega$$

$$u=0 \text{ on } \partial\Omega, \quad (10)$$

where f denotes internal heat sources and q is the spatially varying heat conductivity. If one cannot measure q directly, one can try to determine q from internal measurements of the temperature u or from boundary measurements of the heat flux $$q\frac{\partial u}{\partial n}.$$

Note that (10) with unknown q is nonlinear, because the relation between this parameter and the solution u—that serves as the data in the inverse problem—is nonlinear even if the direct problem of computing u with given q is linear. For this parameter identification problem, the parameter-to-output map F maps the parameter q onto the solution $u_q$ of the state equation (10) or to the heat flux $$q\frac{\partial u}{\partial n}.$$

Thus, computing F(q) means to (numerically) solving (10) with the parameter value q. We will come back to this model problem later.

Neither existence nor uniqueness of a solution to (9) is guaranteed for the problem posed in (10). Assuming for the sake of simplicity that the exact data y are possible (i.e. 'attainable')—i.e., that (9) in fact has a solution and that the underlying model is thus correct—we use a generalized solution concept (see [4] for the general, non-attainable, case): For $x^* \in X$, we call a solution $x^\dagger$ of (9) which minimizes $\|x-x\|^*$ among all solutions an x-minimum-norm solution of (9) (x*-MNS for short). The element x* can and should include available a priori information like positions of singularities in x if they happen to be available.

One main issue in solving an inverse problem (9) is that its solution or solutions do not depend continuously on the data y. This can be seen easily if one considers the one-dimensional version of (10). The one-dimensional version of (10) is $$-(qU')'=f$$

$$U(0)=U(1)=0 \text{ in}[0,1].$$

This can be solved explicitly:

$$\text{For } s \in [0, 1]: \ (-qU')(s) = \int_0^s f(t)\,dt$$

the parameter q in terms of U is obtained via $$q(s) = -\frac{\int_0^s f(t)\,dt}{U'(s)}$$

Consider the effects of small but high frequency oscillations (errors) in the measured data U: such errors in U may lead to arbitrarily large in errors in its derivative U' and hence also in q. In addition, where the temperature gradient U' is close to zero, errors in the source term f and in the integration are heavily amplified since U'→0 is in the denominator of equation.

That issue implies that standard methods cannot solve problems like (9) with discontinuous dependence on data. For the inverse ion channel problem, we will show the discontinuous dependence on data below in examples in Section 5.3. Thus, methods have to be developed which allow the stable solution of (9)—they are called "regularization methods." Regularization methods replace an ill-posed problem by a family of well-posed problems; their solutions, called regularized solutions, are used as approximations to the desired solution of the inverse problem. These methods always involve (a) some parameter measuring the closeness of the regularized to the original (unregularized) inverse problem; (b) rules (and algorithms) for the choice of these regularization parameters. These parameter(s) and rules and algorithms—as well as the convergence properties of the regularized solutions—are central issues in the theory of these inverse methods. The right balance between stability and accuracy is determined by adjusting the parameter(s), rules and algorithms, in order to obtain optimal convergence properties. While the theory of regularization methods for linear ill-posed problems is by now rather comprehensive, it is still evolving and far from complete in the nonlinear case. Indeed, the nonlinear case is so general, that in some sense it can never be complete: one imagines one can always find some nonlinear system and operator with a property not covered by the 'complete' theory. Since the inverse problems involved in our invention are nonlinear, we do not describe the theory of linear inverse problems, but refer the reader to [23].

Those of ordinary skill in the art will appreciate that two widely used methods of regularization are disclosed for solving the present problem. While these types of methods are known and used for other types of problems, they have not been used to solve the problems like the subject of this disclosure.

The following considerations are relevant for both classes of methods. For numerically solving an inverse problem, any regularization method has to be realized in finite-dimensional spaces. In fact, a regularization effect can often be obtained simply by making a finite-dimensional approximation of the problem. The approximation level plays the role of the regularization parameter: at least for linear problems, a projection of an inverse problem into a finite dimensional space makes the problem well-posed (in the sense of continuous dependence of solutions on the data if a suitably generalized solution concept is used). However, these approximate finite dimensional problems become numerically more and more unstable, which is no surprise, since in the limit they approximate an ill-posed problem. Error estimates for the case of noisy data and numerical experience show that at least for severely ill-posed problems, the dimension of the chosen subspace has to be low in order to keep the total error small. Hence, for obtaining a reasonable accuracy, projection methods should be combined with an additional regularization method; e.g., with one of those to be discussed now, see [29, 23, 63].

3.1. Variational Regularization

In general, although mathematicians can solve problems with idealized data, when dealing with systems that are intended to work with measurements obtained from real world instruments, the data y in (9) are not known precisely, but only perturbed ("noisy") data $y^\delta$ are known that are close to the perfect data. The noisy data are separated from the perfect data at most by the norm bound δ:

$$\|y - y^\delta\| \leq \delta \quad (11)$$

The present invention contemplates using variational regularization to identify the structure of existing ion channels, and then to design them. In variational regularization, problem (9) with data satisfying (11) can be replaced by the minimization problem $$\|F(x) - y^\delta\|^2 + \alpha R(x - x^*) \to \min, x \in D(F), \quad (12)$$

with a suitable penalty function R, where $x^* \in X$ is an initial guess for a solution of (9). The most prominent example is "Tikhonov regularization", where $R(x) = \|x\|^2$, i.e., $$\|F(x) - y^\delta\|^2 + \alpha \|x - x^*\|^2 \to \min, x \in D(F) \quad (13)$$

These functionals combine the "residual"—i.e., the output error $\|F(x) - y^\delta\|$—with a penalty term. For Tikhonov regularization, the following holds: for a positive regularization parameter α, minimizers always exist for (13) (under the above-mentioned assumptions) but need not be unique. For that reason, we call any global minimizer of (13) a regularized solution $x_\alpha^\delta$. One can show that $x_\alpha^\delta$ depends continuously on the data for α fixed and that $x_\alpha^\delta$ converges towards a solution of (9) in a set-valued sense with $\alpha(\delta) \to 0$ and $\delta^2/\alpha(\delta) \to$ as δ tends to zero; see [24].

Figure 6:
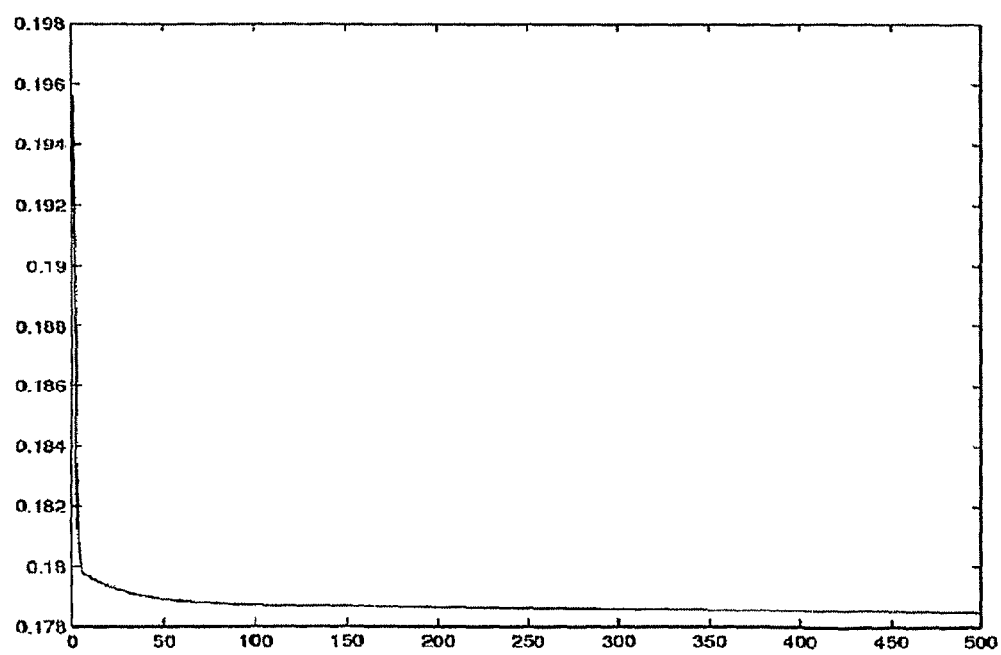
FIG. 6 is a plot of the data propagation error term versus k—this term will go to infinity as k goes to infinity.
Figure 9:
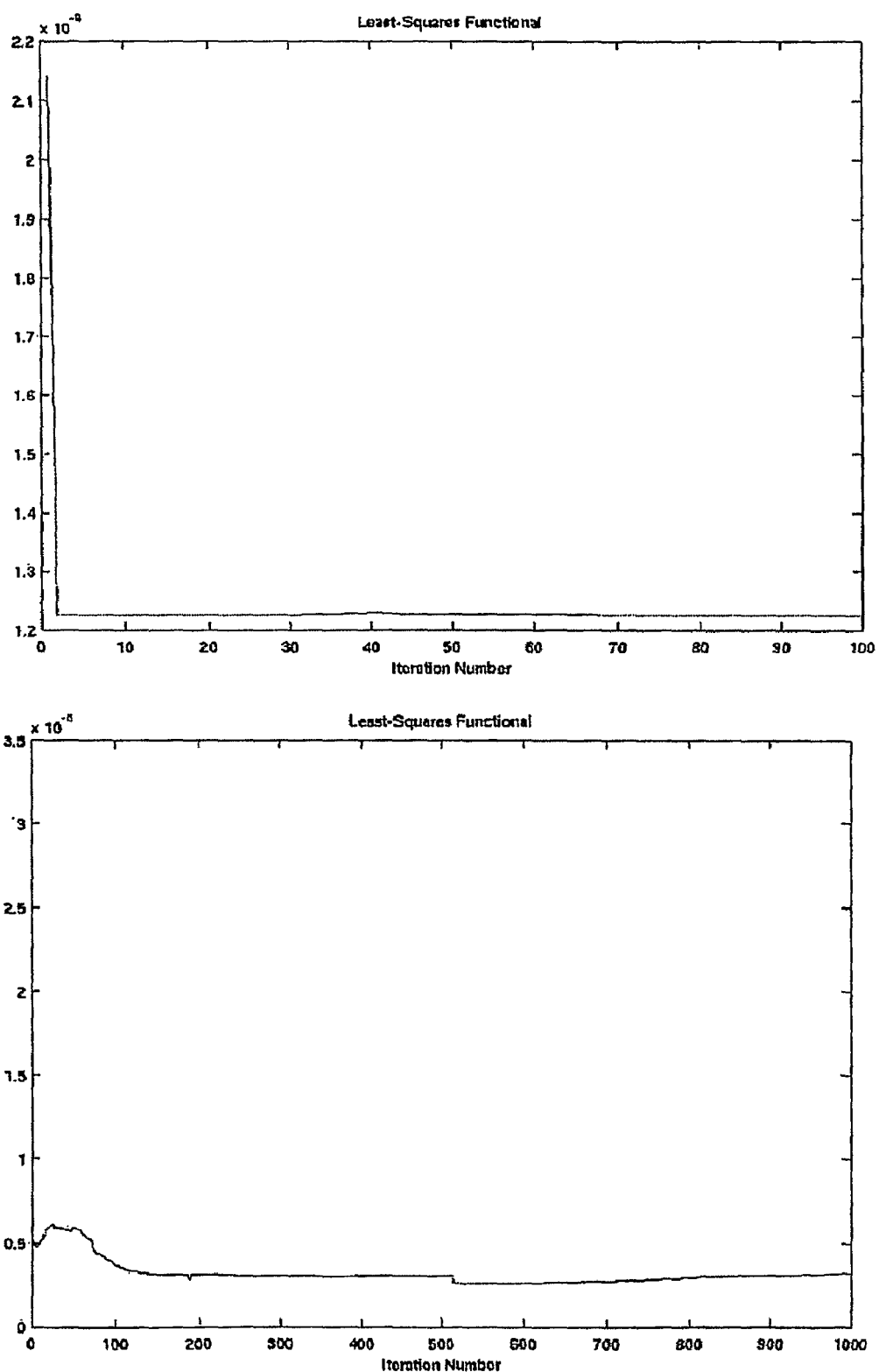
FIG. 9 is a plot of the squared residual $\|F(P_n)-I^\delta\|^2$ as a function of the iteration number for 4×2×2 measurements (above) and 6×3×3 measurements (below).

It is a consequence of the ill-posed nature of the problem that smallness of the residual alone does not imply smallness of the identification error $\|x_\alpha^\delta - x^\dagger\|$, where $x^\backslash$ always denotes an $x^*$-minimum-norm solution $x^*$-MNS of (9); compare also FIGS. 9 with 10 and FIGS. 6 with 7, where the behavior of the residual is compared with the identification error.

Other methods of variational regularization exist besides Tikhonov, and the present invention extends to the use of them as well. A few examples, to which the invention is likewise not limited, of variational regularization include maximum entropy regularization $$\|F(x) - y^\delta\|^2 + \alpha \int_\Omega x(t) \log \frac{x(t)}{x^*(t)} dt \to \min, \quad (14)$$

see [25, 19, 26, 51, 66] or bounded variation regularization $$\|F(x) - y^\delta\|^2 + \alpha \int_\Omega |\nabla x(t)| dt \to \min, \quad (15)$$

which enhances sharp features in x as needed in, e.g., image reconstruction, see [67, 54, 69, 9, 60]. Quite general convergence results about variational regularization can be found in [9, 66].

In any regularization method, the regularization parameter α plays a crucial role. As those of ordinary skill in the art will appreciate, the choice of the weight to give the terms controlled by the regularization parameter represents a compromise between accuracy and stability: if α is too large, the modeling error made by adding a penalty term in (12) leads to a poor approximation. If α is chosen too small, on the other hand, data errors may be immediately amplified too strongly. There are two general classes of options for choosing the parameter: A-priori rules define the regularization parameter as a function of the noise level only, i.e., $\alpha = \alpha(\delta)$, while in a-posteriori rules, α depends both on the noise level and the actual data, i.e., $\alpha = \alpha(\delta, y^\delta)$.

It should be kept in mind that error-free strategies, where $\alpha = \alpha(y^\delta)$ does not depend on δ, cannot lead to convergence (see [23]). This is an asymptotic absolute statement which does not directly apply to the case of finite noise. With finite noise, error free strategies can occasionally lead to good results. As those of ordinary skill in the art will appreciate, care is needed, however, to achieve good results (for finite noise level), because of the lack of an underlying convergence theory (the same is true in the linear case; one can even prove non-convergence). These error-free strategies include the popular methods of generalized cross-validation ([76]) and the L-curve method ([40]); for its non-convergence, see [21] and [75]. Convergence rates and how to choose regularization parameters to obtain optimal convergence rates are questions in applying regularization methods that need to be addressed in solving any inverse problem and certainly this problem concerning ion channels.

Figure 5:
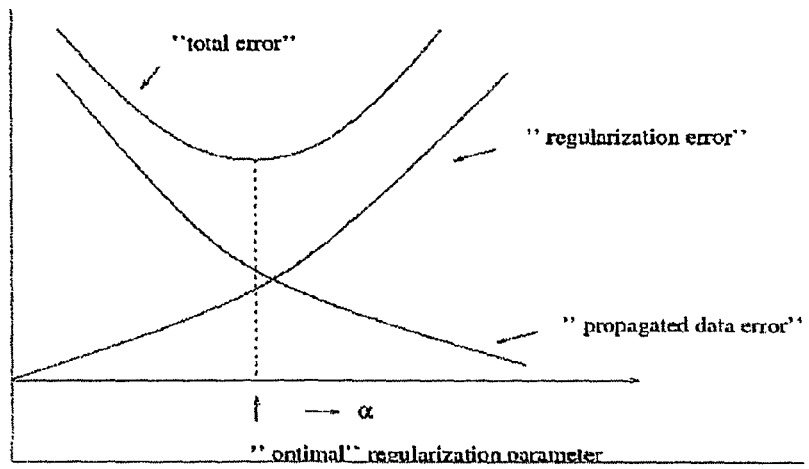
FIG. 5 is a plot of how regularization error and propagated error data combine to provide an estimate of total error.

FIG. 5 illustrates the typical total error behavior of a regularization method. The regularization error, i.e., the error in the solution caused by adding the penalty term in (12), goes to 0 as $\alpha \to 0$, while the propagated data error grows without bound as $\alpha \to 0$. The optimal regularization parameter would be determined by the minimizer of the combined curve in FIG. 5, but is not computable from this curve, since the concrete computation of these curves would require knowing the exact solution of the inverse problem, in which case no further study would be required.

For Tikhonov regularization, a widely used a-posteriori rule is the "discrepancy principle", where $\alpha(\delta, y^\delta)$ is defined as the solution of $$\|F(x_\alpha^\delta) - y^\delta\| = C\delta \tag{16}$$

If this equation (16) has no solution, which my happen for nonlinear problems, it can be replaced by a two-sided inequality. A quite complicated a posteriori strategy that always leads to optimal convergence rates can be found in [71]. The papers quoted above concerning more general variational regularization methods also contains information on suitable strategies for choosing parameters.

With respect to the numerical implementation of Tikhonov regularization (and more general variational regularization methods), one can relax the task of exactly solving problem (13) to looking for an element $x_{\alpha,\eta}^\delta$ satisfying $$\|F(x_{\alpha,\eta}^\delta) - y^\delta\|^2 + \alpha\|x_{\alpha,\eta}^\delta - x^*\|^2 \leq \|F(x) - y^\delta\|^2 + \alpha\|x - x^*\|^2 + \eta \tag{17}$$

for all $x \in D(F)$ with $\eta$ a small positive parameter, see [24]. Tikhonov regularization combined with finite dimensional approximation of X (and of F, see also Section 3.2) is discussed e.g., in [57, 58].

3.2. Iterative Methods

A first candidate for solving (9) in an iterative way could be Newton's method $$x_{k+1} = x_k + F'(x_k)^{-1}(y - F(x_k)), \tag{18}$$

starting from an initial guess $x_0$. Even if the iteration is well-defined and $F'(\cdot)$ is invertible for every $x \in D(F)$, the inverse is usually unbounded for ill-posed problems (e.g., if F is continuous and compact the inverse of F' is also discontinuous). Hence, (18) is inappropriate in this form since each iteration requires one to solve a linear ill-posed problem, which would be unstable, and some regularization technique has to be used instead (see [23] for regularization methods for linear ill-posed problems). For instance Tikhonov regularization applied to the linearization of (9) yields the Levenberg Marquardt method (see [38])

$$x_{k+1} = x_k + (F'(x_k)^* F'(x_k) + \alpha_k I)^{-1} F'(x_k)^*(y - F(x_k)), \tag{19}$$

where $\alpha_k$ is a sequence of positive numbers. Augmenting (19) by the term $$-(\alpha_k I + F'(x_k)^* F'(x_k))^{-1} \alpha_k (x_k - x^*) \tag{20}$$

for additional stabilization gives the iteratively regularized Gauss-Newton method (see [2], [5])

$$x_{k+1} = x_k + (F'(x_k)^* F'(x_k) + \alpha_k I)^{-1} [F'(x_k)^*(y - F(x_k)) - \alpha_k (x_k - x^*)] \tag{21}$$

Usually, $x^*$ is taken as $x_0$, but this is not necessary.

Also, quasi-Newton methods—where F' is suitably approximated—have been developed for ill-posed problems (see [47]). Equations (19) and (21) are based on solving the normal equation of the linearized problem (18), as are most iterative methods for solving the nonlinear ill-posed problem (9)

$$F'(x)^*(F(x) - y) = 0 \tag{22}$$

via successive iteration starting from $x_0$. Equation (22) is the first-order optimality condition for the nonlinear output least-squares problem $$\frac{1}{2}\|y - F(x)\|^2 \to \min, x \in D(F). \tag{23}$$

An alternative to Newton type methods like (19) and (21) are methods of steepest descent like the Landweber iteration $$x_{k+1} = x_k + F'(x_k)^*(y - F(x_k)), \tag{24}$$

see [39], where the negative gradient of the functional in (23) determines the update direction for the current iterate. From now on, we shall use $x_k^\delta$ in our notation of the iterates in order to take into account possibly perturbed data $y^\delta$ as defined in (11).

Figure 7:
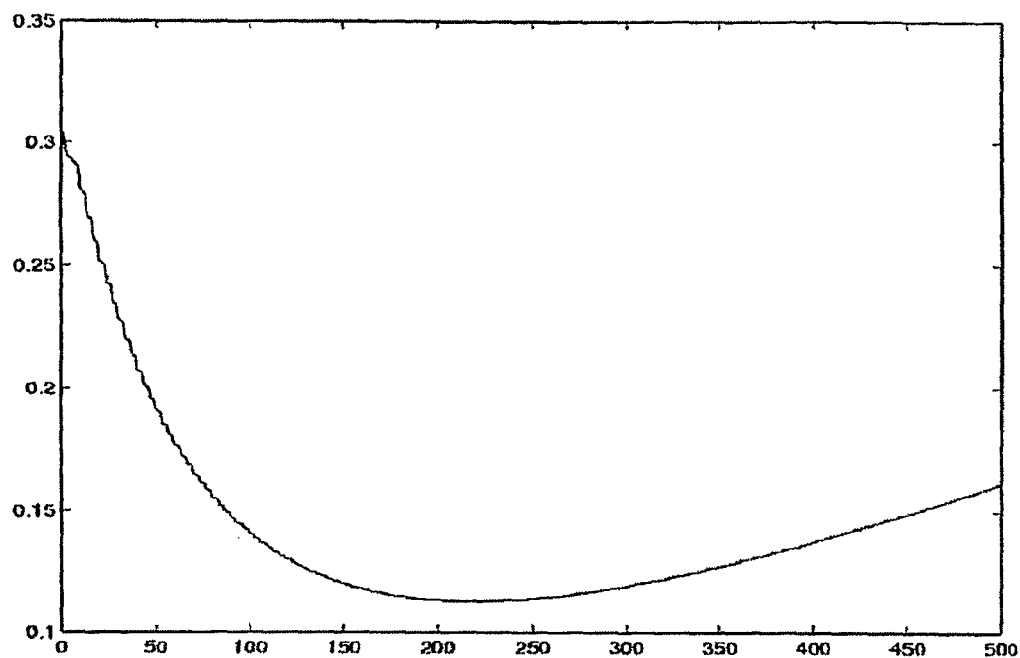
FIG. 7 is a plot of the regularization error term versus k—this term will go to 0 as k goes to infinity.

In the ill-posed case, the iteration must not be arbitrarily continued because of the instability inherent in (9). Terminating the iteration properly is important to all iterative methods. An iterative method only can become a regularization method, if it is stopped "at the right time", i.e., only for a suitable stopping index $k^*$ does the iterate $x_{k^*}^\delta$ yield a stable approximation to the solution $x^\dagger$ of (9). Due to the ill-posed nature of the problem, a mere minimization of (23), i.e., an on-going iteration, leads to unstable results and to the typical error behavior shown in FIGS. 6 and 7. FIG. 6 is a plot of $\|F(x_k^\delta) - y^\delta\|$ vs. k, while FIG. 7 is a plot of $\|x_k^\delta - x^\dagger\|$ vs. k.

While the error in the output decreases as the iteration number increases, the error in the parameter starts to increase after an initial decay. The stopping index plays the role of the regularization parameter.

Again, there are two classes of methods for choosing the regularization parameter, i.e., for the determination of the stopping index $k_*$, namely a-priori stopping rules with $k_* = k_*(\delta)$ and a-posteriori rules with $k_* = k_*(\delta, y^\delta)$. Once more, the discrepancy principle is a widely used representative for the latter a-posteriori rules, where $k_*$ now is determined by $$\|y^\delta - F(x_{k_*}^\delta)\| \leq \tau\delta < \|y^\delta - F(x_k^\delta)\|, 0 \leq k < k_*. \tag{25}$$

for some sufficiently large $\tau > 0$. As opposed to (16) for Tikhonov regularization, (25) now is a rule easy to implement, provided that an estimate for the data error as in (11) is available. The discrepancy principle for determining the index $k^*$ is based on stopping as soon as the residual $\|y^\delta - F(x_k^\delta)\|$ is on the order of the data error, which is somehow the best one should expect: All approximate solutions which give a residual not much larger than the data error are equally good or bad if one has no other information, since the data are also only know within this accuracy. For solving (9) when only noisy data $y^\delta$ with (11) are given, it would make no sense to ask for an approximate solution $\tilde{x}$ with $\|y - F(\tilde{x})\| < \delta$. The price to pay would be instability. Convergence analysis for iterative regularization methods has been a hot topic in research recently, see, e.g., [31], [18], [49].

At first sight, Newton type methods might be thought to converge much faster than Landweber iteration; this is of course true in the sense that an approximation to a solution of (9) with a given accuracy can be obtained by fewer iteration steps. However, a single Newton type methods step (see (19) or (21)) is more expensive than a Landweber iteration (see (24)) and also the instability shows its effect earlier in Newton type methods and so that the iteration has to be stopped earlier. Thus, it cannot be said that Newton type methods are in general preferable for ill-posed problems to the much simpler Landweber method. If especially efficient methods are used to solve the linear problems involved in each step of a Newton iteration, see [6], [12], Newton methods may be preferable but even that is not assured automatically.

Many iteration schemes for solving inverse problems are formulated in terms of the Fréchet derivative and its adjoint operator. There are several notions of derivatives of nonlinear operators; all have in common that they are approximations of the nonlinear operator by linear operators in some "best-possible" way; a convergence theory for direct and inverse problems for nonlinear equations usually requires conditions how this approximation is measured, the simplest and mostly used conditions summarized in the term Fréchet derivative. We show how, e.g., Landweber iteration is realized for the prototype parameter identification problem (10). The ideas presented then also apply in a similar way to other methods as (19) and (21). In a first step, we translate the problem into a Hilbert space framework and therefore consider the underlying partial differential equation in its weak operator formulation $$A(q)u=\hat{f} \qquad (26)$$

with $A(q):H_0^1(\Omega)\to H^{-1}(\Omega)$ and $\hat{f}\in H^{-1}(\Omega)$ defined by $$(A(q)u,v)=\int_\Omega q(x)\nabla u\nabla v dx \text{ and } (\hat{f},v)=\int_\Omega fv\, dx \qquad (27)$$

For a set $D(F) \subset X=H^1(\Omega)$ (with $s>d/2$ where d is the dimension of $\Omega$) of admissible parameters q, the direct problem (26) admits a unique solution $A(q)^{-1}\hat{f}\in H_0^1(\Omega)$ which will be denoted by $u_q$ in order to emphasize its dependence on q. If we regard for simplicity the case of distributed $L^2$-temperature measurements, the parameter identification problem can be put into the form (9) with $$F:D(F)\subset X\to Y=L^2(\Omega),\ q\to Eu_q \qquad (28)$$

and $y=Eu_{q^\dagger}$, where $E:H_0^1(\Omega)\to L^2(\Omega)$ is the embedding operator.

For given $q\in D(F)$, a formal linearization of the direct problem (26) in direction $p\in X$ yields $$A(q)u_qp=-A(p)u_q, \qquad (29)$$

where the right-hand side is due to the linearity of $A(\cdot)$ with respect to q. Therefore, the Fréchet derivative of (28) is given by $$F'(q):X\to Y,\ p\to Eu_qp,$$

where $u_qp\in H_0^1(\Omega)$ denotes the solution of (29), i.e., $$u_qp=-A(q)^{-1}A(p)u_q \qquad (30)$$

Hence, if we build the inner product in (24) with an arbitrary test function $p\in X$, the k-th iteration step becomes (where we omit E for reasons of readability)

$$(q_{k+1}^\delta,p)=(q_k^\delta,p)+(F'(q_k^\delta)^*(y^\delta-u_{q_k^\delta}),p) \qquad (31)$$

$$(q_{k+1}^\delta,p)=(q_k^\delta,p)+(y^\delta-u_{q_k^\delta},F'(q_k^\delta)p)$$

$$(q_{k+1}^\delta,p)=(q_k^\delta,p)-(y^\delta-u_{q_k^\delta},A(q_k^\delta)^{-1}A(p)u_{q_k^\delta}) \qquad (32)$$

Because of $$(y^\delta-u_{q_k^\delta},A(q_k^\delta)^{-1}A(p)u_{q_k^\delta})=(A(q_k^\delta)^{-1*}(y^\delta-u_{q_k^\delta}),A(p)u_{q_k^\delta}),$$

the iteration can also be written as $$(q_{k+1}^\delta,p)=(q_k^\delta,p)-(w_k,A(p)u_{q_k^\delta})$$

$$=(q_k^\delta,p)-\int_\Omega p(x)\nabla w_k\nabla u_{q_k^\delta}dx, \qquad (33)$$

where $w_k$ denotes the solution of the linear adjoint problem $$A(q_k^\delta)^*w_k=y^\delta-u_{q_k^\delta} \qquad (34)$$

Hence, each iteration step in (24) requires solving the direct problem (26) in order to obtain $u_{q_k^\delta}$ and the adjoint problem (34) with the residual $y^\delta-u_{q_k^\delta}$ as right-hand side. Eventually, the update according to (33) can be numerically realized as follows: if $\{p_1, p_2, \ldots, p_n\}$ is an n-dimensional basis of the parameter space $X_n\subset X$ with $q_k^\delta$ denoting the vector representation of $q_k^\delta$, then (33) means to solve the linear system $$Ms_k^\delta=r_k^\delta,$$

where M is the Gramian Matrix $$M(i,j)=(p_i,p_j)$$

and the vector $r_k$ is defined via $$r_k^\delta(j)=\int_\Omega p_j(x)\nabla w_k\nabla u_{q_k^\delta}dx,$$

and to update the parameter via $$q_{k+1}^\delta=q_k^\delta+s_k^\delta.$$

Note that the approach (32) would require to solve n linear problems (29), clearly showing the advantages of (33) which gets by with solving a single problem (34).

Returning to our general discussion, we note that some iterative regularization methods can also be derived from certain initial value problems for abstract evolution equations, which are then in turn called continuous iteration methods. For nonlinear problems, some of these methods are analyzed and related to their discrete analogues (especially (21)) in [1] and [48]. The asymptotic regularization method $$\dot{u}_\delta(t)=F'(u_\delta(t))^*(y^\delta-F(u_\delta(t))), \qquad (35)$$

is studied in the nonlinear setting in [74]; it is also called inverse scale-space method in the context of imaging problems, see [72, 70, 64]. In [52], it is shown that (35) applied to (9), where F is the concatenation of a forward operator and a certain projection operator, can in fact be considered as a level set method. Level set methods, see [61, 73] have been successfully used for shape reconstruction problems e.g., in [68], [62], [8], their role as regularization methods for inverse problems has been analyzed in [7].

4. Regularization of Inverse Ion Channel Problems

As discussed for general inverse problem in Section 1, we consider two classes of inverse ion channel problems which have different practical motivations:

Identification problems determine properties of a "real" channel (permanent charge and structure) from measurements of the channel output (in a standard experimental measuring the total current) at various different conditions (applied voltages, bath concentrations of the ions, types of ions, pH, drugs, modulators). This contrasts with design problems that determine properties of "in-silico" (meaning the result of computations presumably performed in a computer made from integrated circuits in silicon chips) channels constructed to specification. These include, but are not restricted to artificial channels made by site directed mutagenesis from proteins, e.g., by mutating the (nearly) nonselective bacterial protein ompF, or by chemical modification of ompF, or by artificial channels made from in polyethylene terephthalate (PET) abiotic membranes and by chemical (NaOH) etching of ionization tracks produced by heavy ions. Such channels are designed so they have optimal characteristics with respect to some criterion (e.g., selectivity between certain ion species like $Na^+$ and $Ca^{++}$).

The unknowns to be identified or designed are related to the permanent charge, i.e. the ion species that is always confined to the channel because it is part of the channel protein (i.e., covalently linked to the channel protein). First of all, an important number is the total amount of permanent charge, i.e. the number of charged particles confined to the channel. If k is the density of a confined species, then the total number is given by the integral $$N_k = \int_\Omega \rho_k dx \qquad (36)$$

A second important quantity determining the permanent charge is the external constraining potential $\mu_k^0$, which represents the forces acting on the permanent charge that keep it within the channel and thereby encodes this property of the channel structure. In absence of an electrical field and of electrochemical interaction with other ions, the permanent charge density is given by $$\rho_k = c_k N_k \exp(-\mu_k^0/z_k) \qquad (37)$$

with a constant $c_k$ determined from the above integral condition. Hence, the number $N_k$ and the constraining potential $\mu_k^0$ determine the permanent charge $\rho_j$ and subsequently the selectivity properties of the channel. In the solution of the inverse problem, these two quantities lead to a different degree of difficulty. The total charge $N_k$ is a single positive integer number for which an upper bound is available (since too large a number of permanent charges would destroy the channel); thus it could even be determined by sampling all its possible values. The constraining potential $\mu_k^0$ is a function of space, so that an inverse problem of determining the potential has always to be formulated as an infinite-dimensional inverse problem in a suitable function space. Since ill-posedness in the strict sense of discontinuous dependence on data arises only for infinite-dimensional problems and numerical instability becomes more severe as the number of unknowns and/or design parameters in the inverse problems increases (cf. [23], see also the paragraph preceding Section 3.1 above), instability effects are expected to be more significant for determining the constraining potential $\mu_k^0$ than for determining the total charge $N_k$. As a consequence of the ill-posedness, suitable regularization methods have to be used to compute stable approximations of the potential as explained in the previous sections. In the following we will describe the computational solution of the inverse problems of determining total charge and potential in detail, both in the cases of identification and of design. Note that our main interest is in the total charge when doing identification, but we must determine the potential as well to determine the total charge reasonably accurately.

4.1. Identification

The aim of the identification problem is to find one or both of total charge and potential from measurements of the outflow current I taken at different bath concentrations of the mobile ions (boundary values of the densities $\rho_j$) and at different applied voltages (boundary values of the electric potential V) with perhaps different types of ions present as well.

The outflow current is a boundary integral of the total current $J = \Sigma_k J_k$, one real number for each combination of voltage and bath concentrations. The underlying forward model creates a relation between the input $P = (\mu_k^0, N_k)$ and the output I. Since the output I also is a function of voltage and bath concentrations, the input-output relation has to be set up as an operator $F: P \mapsto I$ between function spaces. Note that the evaluation of the operator F for a specific value of P involves the solution of forward problems with given P, for each combination of voltage and bath concentrations. In the idealized setting, this makes an infinite number of forward problems.

The identification problem can be formulated as an operator equation as in (9)

$$F(P) = I^\delta, \qquad (38)$$

where $I^\delta$ denotes the noisy version of the current obtained from measurements. Due to the ill-posedness, the operator equation might not be solvable for noisy data and moreover, the dependence of the solution on the data is discontinuous. Therefore we use regularization schemes to approximate the solution.

One of the most frequently used class of regularization methods for nonlinear problems are variational methods (12)—e.g., Tikhonov regularization (13)—where the inverse problem (38) is approximated by the variational problem $$J_\alpha(P) := \|F(P) - I^\delta\|^2 + \alpha R(P) \to \min_P, \qquad (39)$$

with a suitable regularization functional R and a positive real regularization parameter α. As explained in Section 3.2, an alternative is iterative regularization methods, based on an iteration procedure of the form $$P_{n+1} = P_n - G_n(F(P_n) - I^\delta), \qquad (40)$$

with a linear or even nonlinear operator $G_k$ depending on $P_k$ in general. The regularization parameter for an iterative scheme is the stopping index $n_*$. The iteration is continued until n reaches its stopping value $n_*$. We mention that an analogous iteration method can be used to solve the variational problem appearing in variational methods.

In practice, one has to discretize the function I of the bath concentrations and voltages, so that one only computes a finite number M of function evaluations, denoted by $I_1, \ldots, I_M$, and the operator F can be written in the form $F = (F_1, \ldots, F_M)$. The evaluation of a single part $F_j$ amounts to a single solution of the forward problem for a specific combination of the bath concentrations and the applied voltage, and the subsequent computation of the outflow current from the solution.

In our test example we carried out a gradient-based method, which is an iteration procedure of the form $$P_{n+1} = P_n - \tau_n [F'(P_n)^*(F(P_n) - I^\delta) + \alpha R'(P_n)] = P_n - \tau_n J_\alpha'(P_n), \qquad (41)$$

which can be interpreted as a minimization method for the variational problem (39) or, with α=0 and an appropriate choice of the stopping index, as an iterative regularization method of the form (40), namely the Landweber method (24). Here F', R', and $J_\alpha'$ denote the derivatives of the operator F and the functionals R and $J_\alpha$, respectively, in the appropriate function spaces. Moreover, $F'(P_n)^*$ is the adjoint of the derivative (which is a linear operator between these function spaces).

The simplest, but already relevant, inverse problem to be solved in this context is to determine the number $N_k$ characterizing the total permanent charge (i.e., $P = N_k$ in the above setting). As noticed above, this problem is one-dimensional as an inverse problem (although, of course, the direct problem is still a system of partial differential equations) and hence, the instability is expected to be less pronounced. Also, this problem is not very challenging with respect to the optimization algorithm. The main issue in the optimization is the evaluation of the functional $J_\alpha$ and the concomitant regularization of the operator F, which involves the solution of several forward problems. Since the implementation of the adjoint operator $F'(P_n)^*$ is a complicated task we approximated the gradient by finite differences $$P_{n+1} = P_n - \frac{\tau_n}{\varepsilon}(J_\alpha(P_n + \varepsilon) - J_\alpha(P_n)), \quad (42)$$

for $\varepsilon$ sufficiently small. This means that each iteration step requires two evaluations of the functional $J_\alpha$, and consequently the solution of 2M forward problems. Since the aim is to identify a single real number only, it seems reasonable that this is possible for M rather low, and indeed our computational experiments indicate that this is possible with high accuracy for M=10 and even for M=5.

The next level with respect to complexity is the identification of the constraining potential $\mu_k^0$, which keeps the permanent charges within the channels and so is closely related to the distribution of those charges within the channel. This problem turns out to be severely ill-posed so that regularization is of fundamental importance. In our computational tests we use iterative regularization as outlined above with the discrepancy principle as a stopping rule, i.e., the iteration is stopped when the residual reaches the order of the noise level. For the implementation of the method, an additional discretization of the constraining potential is needed, which we also perform by piecewise linear functions. The computational complexity of this inverse problem is much higher also due to the fact that a much higher value $\overline{M}$ of different setups is needed in order to obtain a reasonable reconstruction of the potential $\mu_k^0$.

We mention that inverse problems for PNP-systems modeling semiconductor devices have been considered before (cf. [10, 11] and the references cited there). However, there are many fundamental differences to the case of PNP models for ion channels. First of all, in semiconductor models all chemical interactions are ignored, i.e., the excess energy term $E^{ex}$ and the corresponding potential are ignored. Moreover, there are several other differences in the models, e.g., in semiconductors there are at most two different charged species, one of them negative and one positive (electrons and holes) and no uncharged species in semiconductors, whereas a reasonable ion channel has at least three different charged species, and therefore two with same sign. A fundamental consequence of these effects is the absence of selectivity in semiconductor devices, which on the other hand is the most attractive property of ion channels as technological devices. There are also several significant differences in the identification process. In particular not only measurements of currents but also of capacitances can be used to identify and design semiconductor devices, and on the other hand only the applied voltage can be varied in semiconductor devices. (There is no equivalent of varying bath concentrations.) Since the measured currents and capacitances are functions of a single variable—the voltage—in semiconductors, the evaluation of the forward map F involves significantly fewer solves of the PNP-system (1), (2), and consequently the computational complexity of the identification problem for semiconductors is by far lower than for ion channels, though still huge compared to many other inverse problems.

4.2. Design

The general remarks and notations of Section 4.1 are also valid here. However, as explained above, in the case of (optimal) design there is an objective to be achieved instead of an equation to be solved. In the applications to ion channels we have in mind, the prime objective is to increase selectivity of one species over another. As discussed in detail in [33], selectivity has to be defined by its dependence on experimental measurements of particular currents and or electrical potentials, and several different selectivity measures are available. A selectivity measure $S_j$ of a species can be defined as a functional of ion densities and fluxes (possibly at varying voltage, see [33]). Since the densities and fluxes depend implicitly on the unknowns P related to the permanent charge (either the total number of charges or the constraining potential), the selectivity measure can also be rewritten as a functional $S_j = S_j(P)$ of these parameters. If the aim is to increase selectivity of species a over b, which is frequently the case, then one can minimize a relative selectivity measure $$Q(S_a(P), S_b(P)) \to \min_P, \quad (43)$$

A choice which we also use in our computational experiments is the selectivity quotient $Q(S_a, S_b) = -S_a/S_b$. (Note that minimizing the negative quotient is equivalent to the original aim of maximizing the relative sensitivity). Analogous treatment is possible for other choices of Q, e.g., $Q(S_a, S_b) = -S_a/S_b$ or $Q(S_a, S_b) = -S_a + S_b$.

Like identification tasks, significant instabilities appear also in the optimal design tasks. In this case there is no input data, but if one minimizes a functional Q as above, then first of all the minimizer might not exist, which makes the norm of P tend to infinity in a minimization algorithm. Even if a minimizer exists, it is not robust with respect to small perturbations of the problem (small changes of applied voltage and concentrations, modeling errors, numerical errors, . . . ), so that a computed solution becomes useless in practice.

To overcome the instabilities, similar regularization approaches as described above have to be used. In an analogous way one can define variational and iterative regularization methods by just changing the objective functional to Q. In our computational tests, we specifically use a variational method of the form $$Q(S_a(P), S_b(P)) + \alpha \|P - P^*\|^2 \quad (44)$$

where P* is an a-priori guess. In an in-silico ion channel this a-priori guess could introduce additional criteria into the minimization, e.g., P* can represent a total charge or a potential that is easy to manufacture, so that the regularization term would introduce a criterion for the minimizer to be close to easily manufacturable states. For example, the minimizer can constrain the solution to be near an existing known ion channel in order to facilitate manufacture from a known starting point. In this way robustness is introduced to the problem, which can also be observed in the results of our computational experiments.

From a computational viewpoint, the minimization of the regularized variational problem is an analogous task to the minimization appearing in identification problems. The main steps are the evaluation of the objective functional (by solving forward problems and subsequently evaluating selectivity measures) and the computations of gradients of the objective functional with respect to P. The latter task can again be carried out by finite differencing, which reduces to additional solves of the forward problem and creates a high computational effort, or by solving appropriate adjoint problems. The total computational effort for solving optimal design problems is usually much less than for solving identification problems, since the selectivity measure is only computed for very few different combinations of bath concentrations and voltages, so that significantly less forward problems have to solved for evaluating the objective functional than in the case of identification.

We finally mention that optimal design problems for PNP systems have also been investigated before in applications to semiconductor devices (cf. [42, 43, 13]), but again there are many significant differences to the case of ion channels. Besides all the differences in the forward problem, the optimal design of semiconductors (and in particular the objective functional) is always related to currents, there is no analog of a selectivity measure in semiconductors. Hence, the optimal design task for ion channels is a completely new problem that connects only loosely to previous literature.

It should be noted that a significant difference between the tasks of identification and design is that any freedom in the solution tends to be undesirable in the identification problem where accuracy is highly valued. On the other hand, in the design task freedom is desirable because it allows a range of possibilities for optimizing manufacturability.

5. Proof of Concept

In order to verify that the proposed approach works in concrete and biologically relevant applications, we disclose examples related to L-type Ca channels. L-type Ca channels (abbreviated LCC below) are a desirable place to start work in this field, because they are one of the most well investigated channel types and moreover, the forward models we use have been calibrated well against real-life experiments (cf. [34, 35]). The forward problem here is directly relevant to the function of L-type calcium channels. The forward problem calculates the current carried for each mobile ion species, and of course the total current through the channel for a given potential and set of concentrations. Thus, the forward problem calculates the selectivity of the channel. Because the amount of calcium current (in particular) through the L-type calcium channel is a direct determinant of the contraction of the heart, and thus the pumping of blood, the forward problem allows control of a biological and medical system of great importance. The specific solution clearly shows the feasibility of our approach.

5.1. Forward Model

The forward model of the L-type Ca channels involves the electrical potential V and five densities $\rho_k$ modeling the five different species $Ca^{++}$, $Na^+$, $Cl^-$, $H_2O$, and half-charged oxygens, the latter corresponding to the permanent charge. This means that each forward problem consists of a coupled system of six partial differential equations, the Poisson equation (1) and five Nernst-Planck equations (2) for the densities $\rho_1, \ldots, \rho_5$ (see Table 1 for the assignment of densities to the species).

Figure 18:
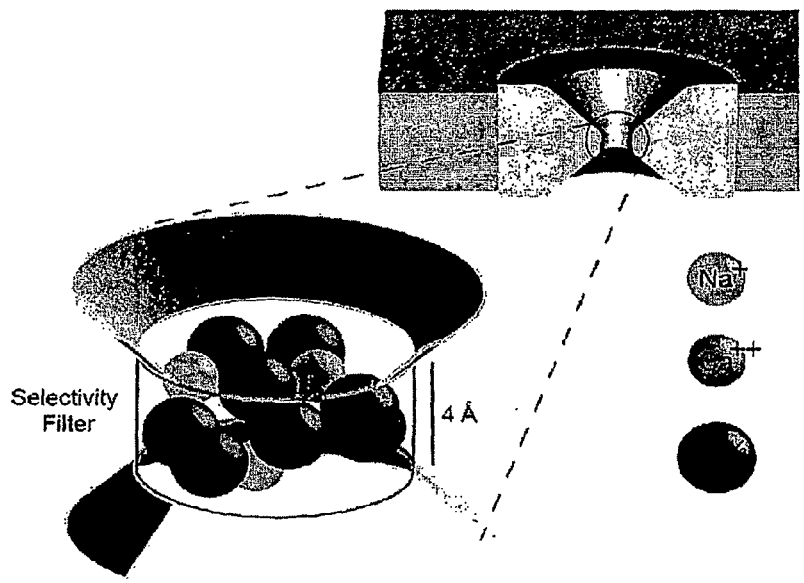
FIG. 18 illustrates the relationship of the permanent charge region to the ion channel as a whole.
Figure 19:
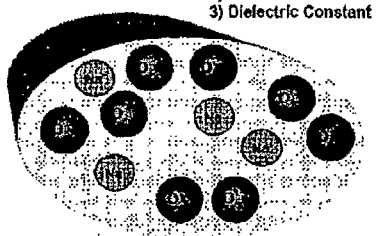
FIG. 19 illustrates the positioning of possible ions in an example permanent charge region of an ion channel.
Figure 19:
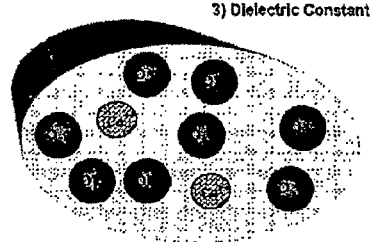
Figure 20:
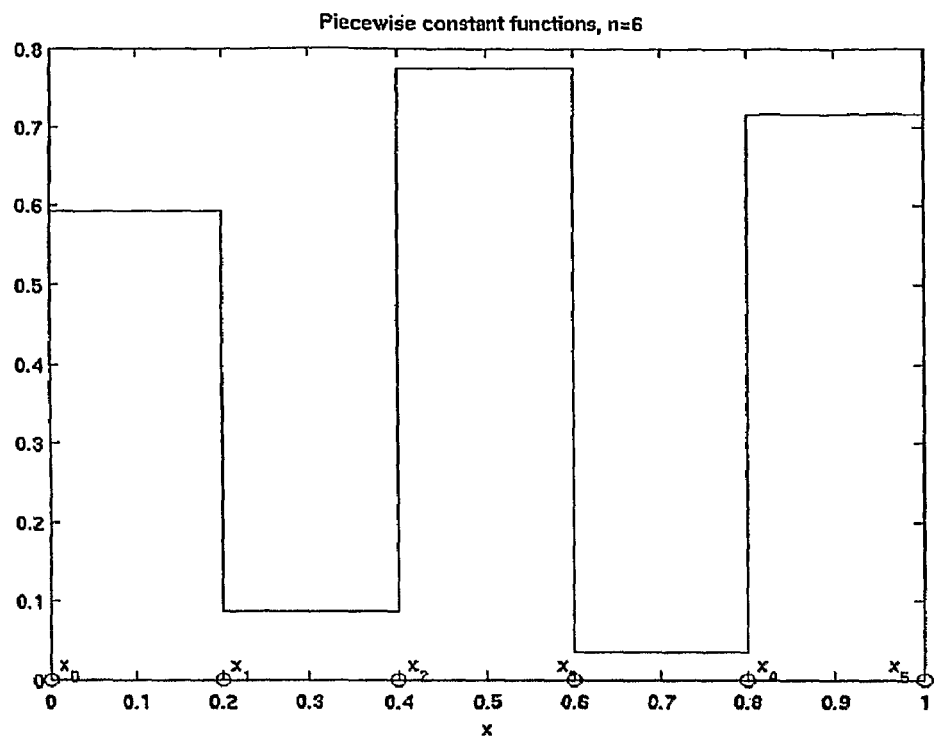
FIG. 20 illustrates an application of piecewise constant functions which are constant within an interval to model the electrical potential and flux region by region.
Figure 21:
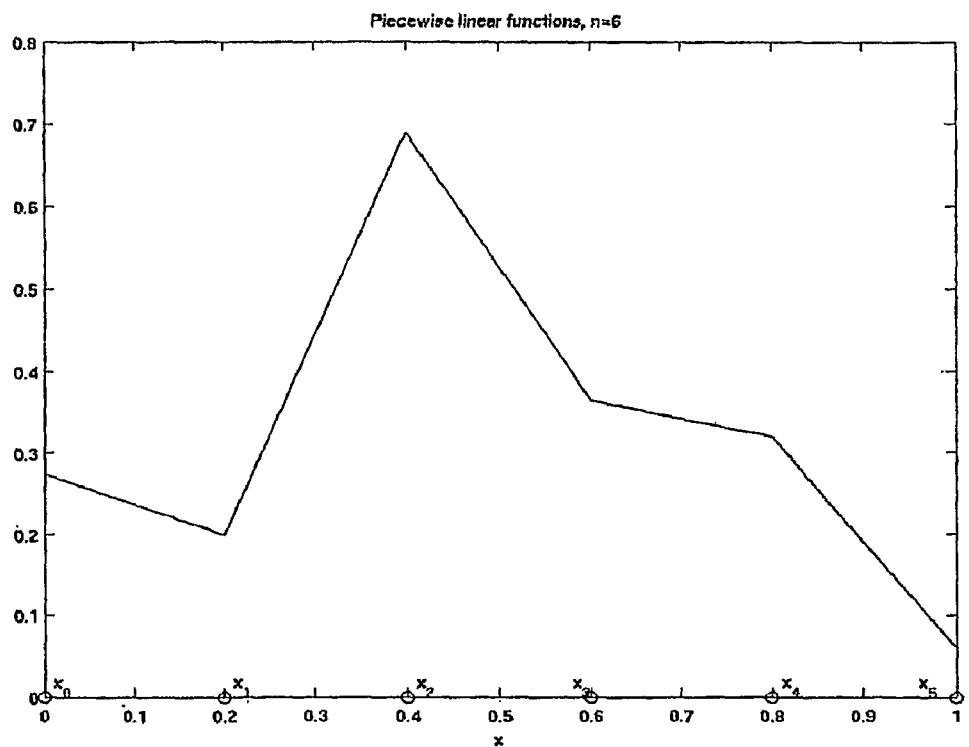
FIG. 21 illustrates an application of ramped linear functions that form a continuous series of ramps to model the electrical potential and flux region by region.

The channel is modeled as cylindrical with radius 0.4 nm (y-z plane) and length 1 nm (x-direction), embedded in two baths both of length 1.7 nm. This yields a total length of 4.4 nm for the system, and therefore the computational domain is chosen as (−L, L) with L=2.2 nm. FIGS. 18 and 19 are sketches of the system geometry. FIG. 18 illustrates the role that the charge-crowded region plays in an ion channel, and FIG. 19 illustrates how differently sized ions interact with the charge-crowded region.

TABLE 1

Parameter Settings for the L-type Ca channels Example using elementary charge $e = 1.602 \times 10^{-19}$ C.

| | k = | | | | |
|---|---|---|---|---|---|
| | 1 | 2 | 3 | 4 | 5 |
| Species = | $Ca^{++}$ | $Na^+$ | $Cl^-$ | $H_2O$ | $O^{-1/2}$ |
| Charge $z_k$ | 2e | e | −e | 0 | −e/2 |
| $\rho_k(L)$ | 6 mM | 12 mM | 24 mM | 55 M | 0 M |

From the geometry of the system it is rather obvious that the flow arises in the x-direction (down the center of the channel), and the model can be reduced by averaging in the y-z plane to a one-dimensional problem with single spatial variable x; but note that our procedures are in no way restricted to the one-dimensional case. In this averaging procedure the shape of the channel has to be taken into account, which yields some spatially dependent coefficients in the reduced system of one-dimensional differential equations. The details of the averaging and an exact statement of the equations to be solved for the L-type Ca channels example are given in Appendix I.

We solve the forward problem on a regular grid with n=1251 (for data generation) and n=1000 cells (for the inverse problem) with a standard conforming finite element discretization of the electric potential and the Poisson equation, and a mixed finite element discretization of the continuity equations for the five species (ions and water). This means we choose points $x_j=j/(n−1)$ for $j=0, \ldots, n−1$ as the grid, and then approximate the electric potential V as well as the fluxes $J_k$ by continuous functions that are linear in each of the intervals $(x_j, x_{j+1})$. The densities $r_k$ and potentials $m_k$ are approximated by functions that are continuous in each of the intervals $(x_j, x_{j+1})$. Since we have the electric potential and 5 different species (water, $Ca^{++}$, $Na^+$, $Cl^-$, Oxygens, each indicated with a respective value for the species index, k), this yields 1252+5×1251=7507 (for data generation) respectively 1001+5×1000=6001 (for the inverse problem) degrees of freedom in the forward problem.

The measurements are the currents, taken as functions of the voltage and of the left bath concentrations $\rho_k(−L)$ for k=1, 2, whereas the right bath concentrations $\rho_k(L)$ are kept fixed. The water concentration is fixed in both baths, and due to the confinement in the channel, $\rho_5(\pm L)=0$. The concentrations $\rho_3(\pm L)$ are finally determined from the charge neutrality $\Sigma_k z_k \rho_k(\pm L)=0$. The parameter settings for the boundary values are given in Table 1, the values of $\rho_k(−L)$ are varied in the identification process.

Drawings 20 and 21 show different approximations to the electrical potentials and fluxes. Note that these functions must be continuous within the intervals but they can be discontinuous at the boundaries of the intervals. Two different functional forms are shown that can be used to describe each of the spatial functions (densities and potentials) but with different parameters of course.

Two are rectangular functions that are constant within each interval and discontinuous at the edge of the intervals. Two are 'ramp' functions that are linear (slope not equal to zero) within the intervals but continuous at the edge of the intervals.

The slopes of course are discontinuous at the edge of the intervals in the latter case.

5.2. Identification I: Reconstruction of the Total Charge

In this case one assumes that the structure of the channel is known, but the total charge of the crowded elements in the selectivity filter is unknown. The inverse problem consists of identifying the total charge based on measurements of the total current for different bath concentrations of the ions. As indicated before, the reconstruction of the total charge is the simplest case of an inverse problem for ion channels, so that we expect more accurate results than for the more complicated inverse problems in the sections below.

This inverse problem is a finite-dimensional one. The aim is to identify a single real number from a finite number of measurements. As mentioned above, this inverse problem is not ill-posed in the classical sense of inverse problems theory, see [23], because of the low dimension. The only possible instability is due to nonlinearity effects, but such effects did not appear in computational tests. In many applications the total charge is the most important single variable so the stability is an advantage of some practical significance.

To test the inverse problem technique for ion channels, we generated synthetic data for the setup as used in the L-type calcium channel calculations [35], i.e., a crowded charge consisting of 8 half-charged oxygens. This means we solve the forward problem with the finer grid and then compute the resulting currents. Subsequently, synthetic noise perturbs the synthetic measurements to provide test data for solving the inverse problem (the same technique is also used for the other inverse problems below). In this way a known reference solution is provided and can be checked to see if the algorithm yields reasonable reconstructions in a stable way.

The reconstructions were carried out by a gradient method for the associated least-squares functional describing the residual. The gradients are approximated by finite differences. This is for illustration only; more efficient ways for approximating the gradient here and for related problems are possible, e.g., via adjoint problems. This approach has been illustrated for the model problem 10 in Section 3.2.

Figure 8:
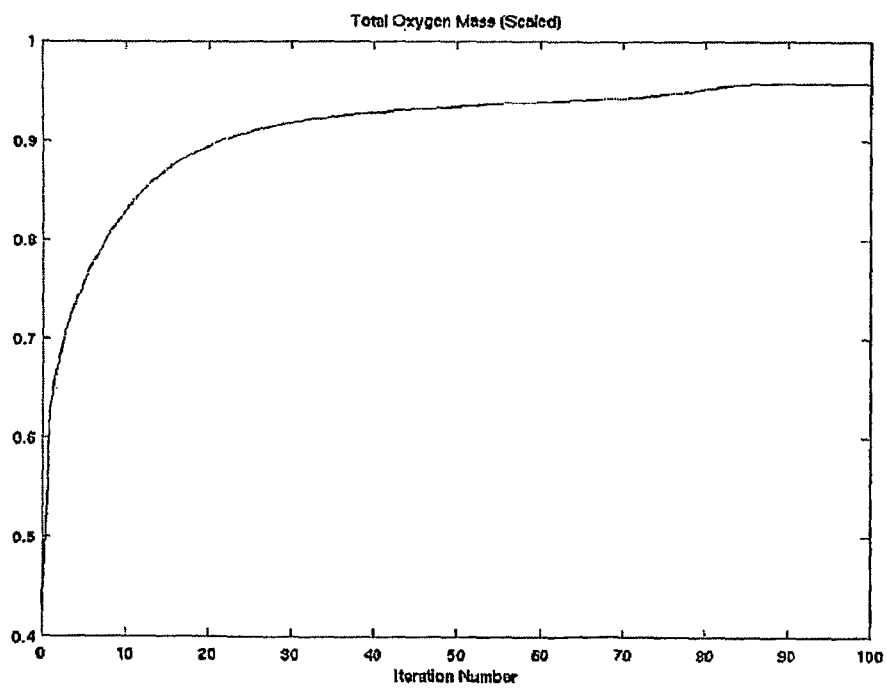
FIG. 8 is a plot of the total charge (relative to the exact value) during the iterations of the gradient method.

In this case reconstructions of the exact total charge are very accurate even for noisy data and even for a rather low number of measurements. A typical test setup used 3 different applied voltages (0.1 V, 0V, −0.1 V), and 2 different concentrations for Na and Ca (2 mM and 4 mM) in the left bath. With all combinations, this gives 3×2×2=12 measured values, i.e., the problem is already overdetermined. The noise level in this case is 0.1% corresponding to the noise level found in actual experiments. An illustration of the reconstruction process in this situation is given in FIG. 8. Here the reconstructed mass of the crowded particles (scaled by the mass of the 8 half-charged oxygens in the real structure) are plotted vs. the number of iterations in the optimization method. In this case a standard stopping criterion would stop between iteration number 90 and 100. The reconstruction does not change significantly afterwards. The difference between the scaled mass of the real total charge and the reconstructed one is less than 5%, although the initial value is quite far away from the solution. Similar behavior was found also in other tests with different initial values and parameter settings.

5.3. Identification II: Reconstruction of the Structure

The second inverse problem is related to the reconstruction of the structure of the channel. This is done indirectly by identifying the constraining potential acting on the crowded ions (oxygens in our example), which models the way the structure interacts with the channel.

The unknown in the above setting is given by $P=\mu_5^0$. Now the inverse problem is to find a space-dependent function on the channel region, which is really an infinite-dimensional problem and can be argued to be ill-posed (this has been done for related (simpler) problems in semiconductors by the authors before, cf. e.g., [11]).

In an idealized setting the unique reconstruction of the constraining potential (as a function of space) would require an infinite number of measurements. Therefore any measurement realized in practice (where of course only a finite number of measurements can be taken) has to be interpreted as a discretization of the problem with infinite number of measurements. It therefore seems obvious that a higher number of measurements yields better reconstruction and this is also confirmed by all our tests. On the other hand a much higher number of measurements yields an extremely high computational effort.

In the solution of the identification problem we use the a-priori knowledge that the variation of the constraining potential $\mu_5^0$ has a significant influence only in the channel region, and therefore approximate it by a constant function in the baths. Note that due to the large values of $\mu_5^0$ in the bath regions the concentration $\rho_5$ is almost zero there in any case. As a consequence, the degrees of freedom of the potential are concentrated in the channel region, and for computational purposes we discretize $\mu_5^0$ as a piecewise constant function on a grid over the channel region (with 11 degrees of freedom in the computations reported below).

Figure 10:
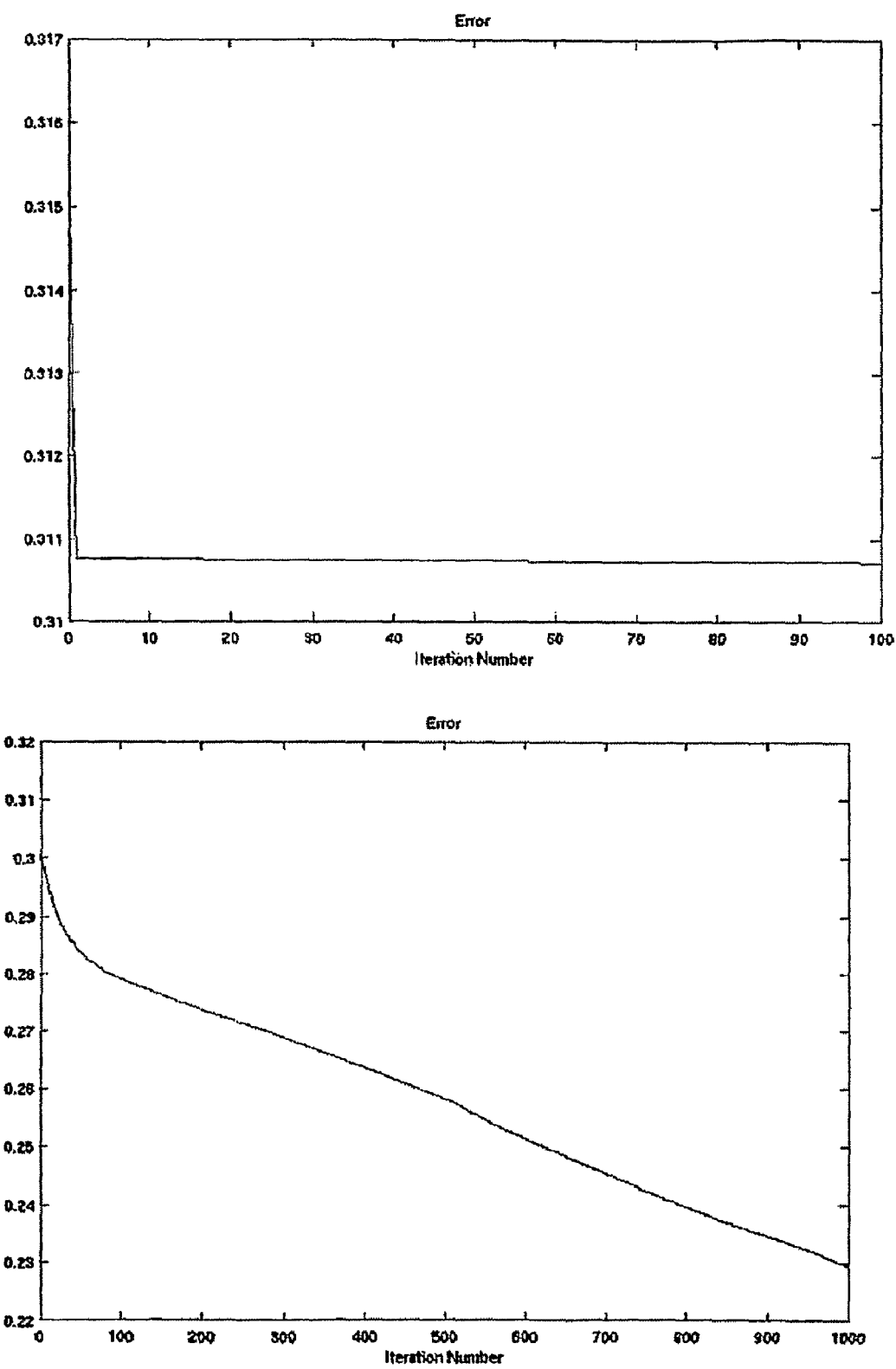
FIG. 10 is a plot of the identification error $\|P_n-P^\dagger\|$ as a function of the iteration number for 4×2×2 measurements (above) and 6×3×3 measurements (below).
Figure 11:
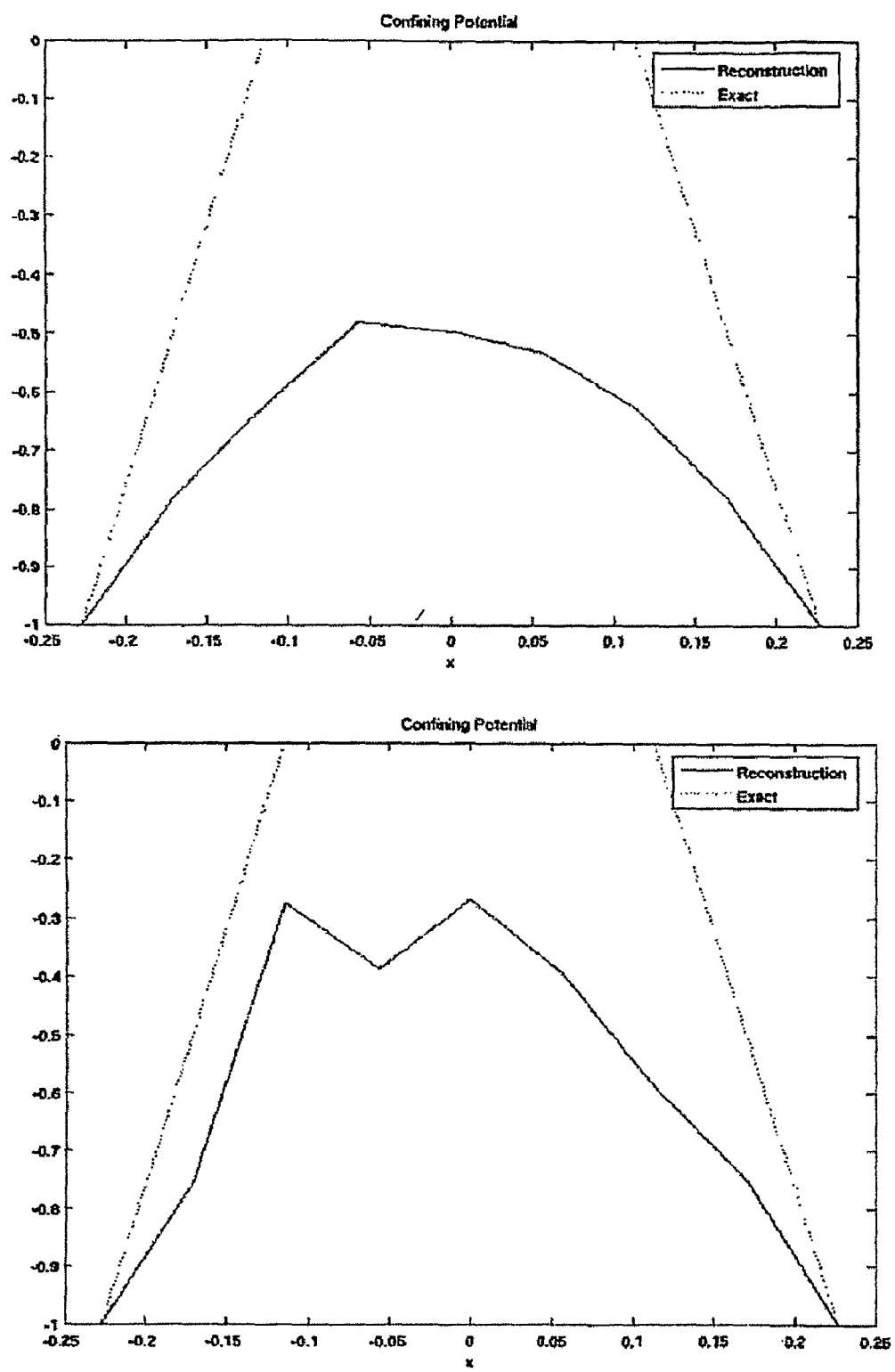
FIG. 11 are the final reconstructions $P_n^*$ obtained at the stopping index determined by the discrepancy principle for 4×2×2 measurements (above) and 6×3×3 measurements (below).
Figure 12:
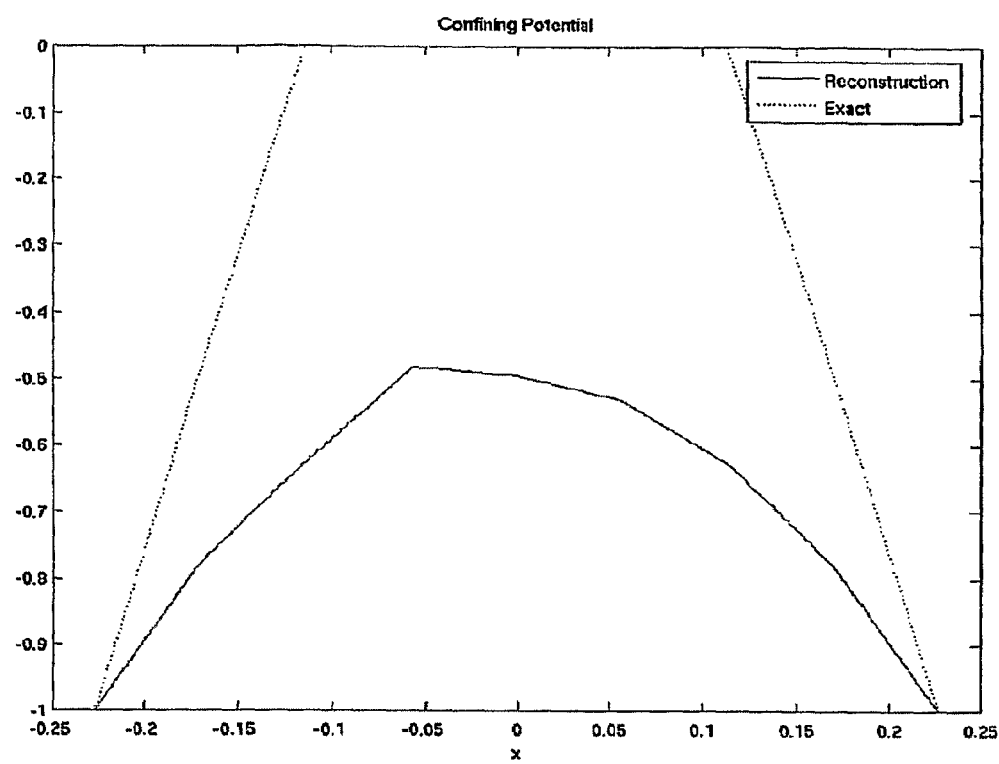
FIG. 12 shows the initial value $P_0$ used for all reconstructions of potentials.

As representative examples of the behavior of the reconstructions we illustrate the results for:

4 applied voltages, 2 different left bath concentrations for Na and Cl, total 4×2×2=16 measurements (Voltages ±10 mV, ±5 mV, and concentrations 2 mM, 4 mM); and 6 applied voltages, 3 different left bath concentrations for Na and Cl, total 6×3×3=54 measurements (Voltages ±10 mV, ±6.6 mV, ±3.3 mV, and concentrations 2 mM, 4 mM, 6 mM); obtained with 0.1% noise. The resulting evolution of the least-squares functional during the iteration is plotted in FIG. 9 (left for case (a) and right for case (b))—one observes they are quite similar in the two cases, the residual decreases to some value around the size of the noise level. As has to be expected from the discussion in Section 3.2 (cf. FIGS. 6 and 7), the evolution of the reconstruction error, however, is completely different, as one can see in the plots of FIG. 10 (left for case (a) and right for case (b)). In the first case (16 measurements) the reconstruction error is hardly reduced, while in the second case one already obtains a very significant decrease before the noise level is reached. This can also be seen from the final reconstructions obtained with a stopping of the iteration dependent on the noise, which are shown in FIG. 11, plotting the negative potentials for illustration purpose, left for case (a) and right for case (b). The initial guess used in both cases is shown in FIG. 11. One observes that the second reconstruction is already rather close to the real potential, in particular in the left part of the channel. The reason for the better reconstruction in the left part is that the concentrations are varied in the left bath, so there is more sensitivity with respect to the data in this region.

Figure 13:
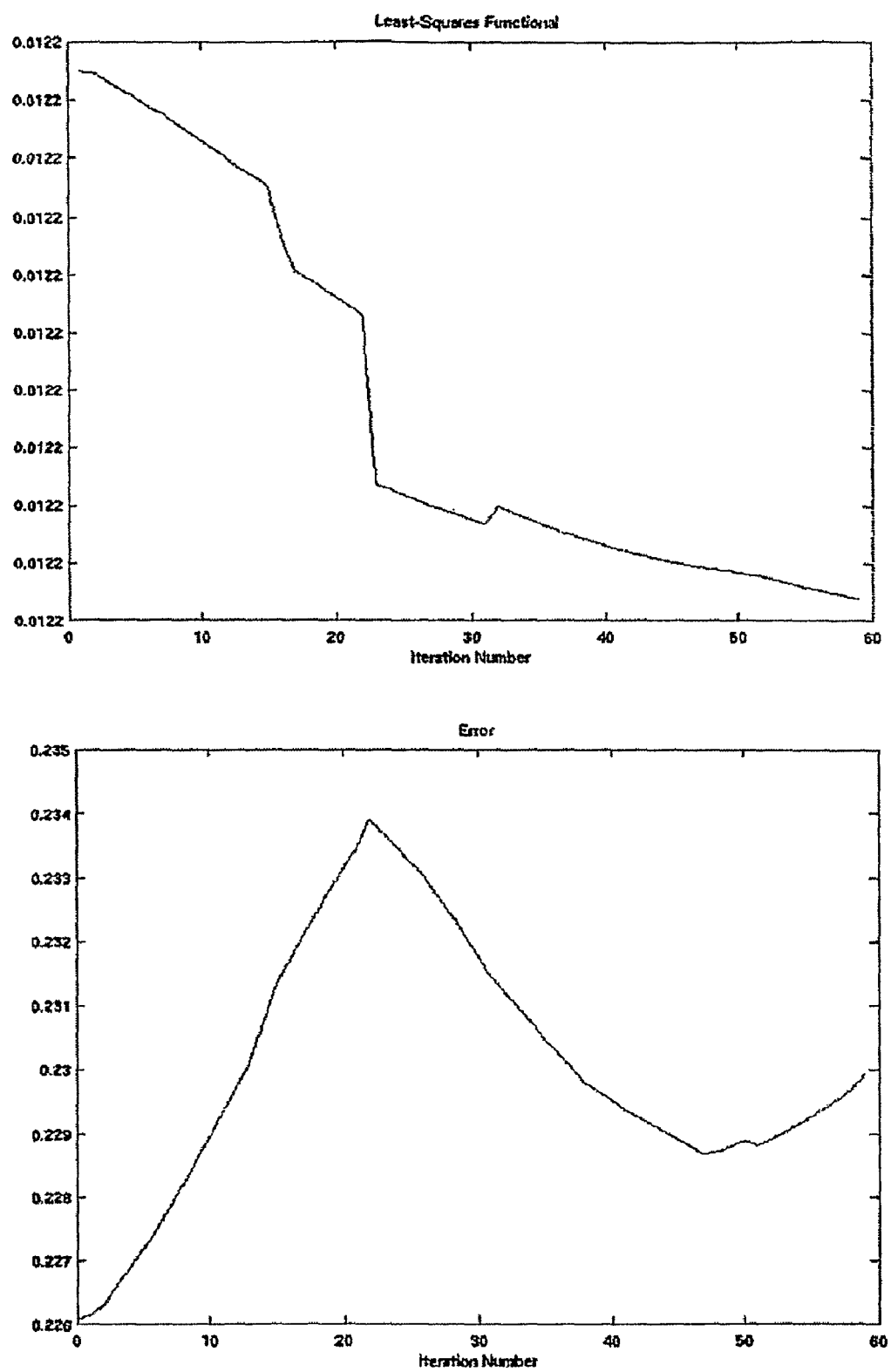
FIG. 13 is a plot of the residual (above) and identification error $\|P_n-P^\dagger\|$ (below) as a function of the iteration number without regularizing stopping criterion.

These results clearly indicate that the reconstructions will improve with increasing number of measurements. For a very high number of measurements, the computational complexity of the inverse problem dramatically increases and it will be necessary to implement very efficient ("adjoint") methods to compute reconstructions The instability of the identification problem in this case is illustrated in the plots of FIG. 13. Here we use the same setup as before (6×3×3 measurements), but a slightly higher noise level (1%). We start with an initial guess where the residual is in the order of the noise level; in such a situation, a stopping rule for an iterative regularization such as the discrepancy principle (cf. Section 3.2) would immediately stop the iteration. If one iterates further (which one would do when using a standard optimization stopping criterion based on the gradient of the residual), then the error starts to increase (and then possibly oscillates) although the residual is still decreasing. This situation is illustrated in FIG. 13, where the least-squares functional and the error are plotted as functions of the iteration number. One observes that in this case the least-squares functional is still decreasing, but the error to the exact solution can increase. Note that this effect did not appear in the examples with a stopping criterion based on regularization theory as described in Section 3.2 (compare also FIGS. 9 and 10 to FIGS. 6 and 7), which again illustrates the importance of regularization.

5.4. Design: Maximizing Selectivity

The optimal design problem has yet to be considered, which aims at designing in-silico channels with at least improved sensitivity compared to a given initial design but possibly also close to a pre-existing ion channel, which can be used as an optional, additional constraining criterion. As a test case to preliminarily assess the techniques disclosed one of the three selectivity measures of the classical literature of electrophysiology can be used: [92], described and analyzed in [33], the so-called permeability ratio, at equal concentrations for all ions in the left and right bath (for this sake we use the bath concentrations $\rho_k(\pm L)=20$ mM for k=1, 2 and $\rho_3(\pm L)= 60$ mM). More precisely, the selectivity measure is the permeability ratio for $Na^+$ and $Ca^{++}$, where the permeabilities on the right side of the channel are computed (detailed formulas for the computations of the permeabilities $S_a$ are given in the appendix). The unknown to be designed is again related to the structure of the channel, i.e., we set $P=\mu_5^0$ and use the same discretization as in the previous section.

The design goal is to maximize or at least increase the sensitivity to a larger value. The present disclosure uses the negative permeability ratio as an additional regularization term, i.e., the objective is changed to the Tikhonov functional arising as a special case of (44)

$$J_\alpha(P) := -S_{Na}(P)/S_{Ca}(P) + \alpha\|P - P^*\|^2 \to \min_P, \quad (45)$$

where $P=\mu_5^0$ is the potential to be optimized and $P^*$ is the initial guess of the potential (the one used in the simulations in [33]). Besides its regularizing effect, the second term in the objective favors solutions as close as possible to the initial guess, which helps to obtain potentials that can be realized in practice. It should be clearly understood that attempts to maximize or improve selectivity by objective computation or by 'hand tuning' will generally be unstable and therefore nearly useless if they do not include a regularization term. The difficulties in protein design 'by hand' are known to those of ordinary skill in the art.

The objective functional is then minimized with a gradient method and suitable step size selection to guarantee decrease of the objective. The gradients are again approximated by finite differences (see above for a discussion of this point).

Figure 15:
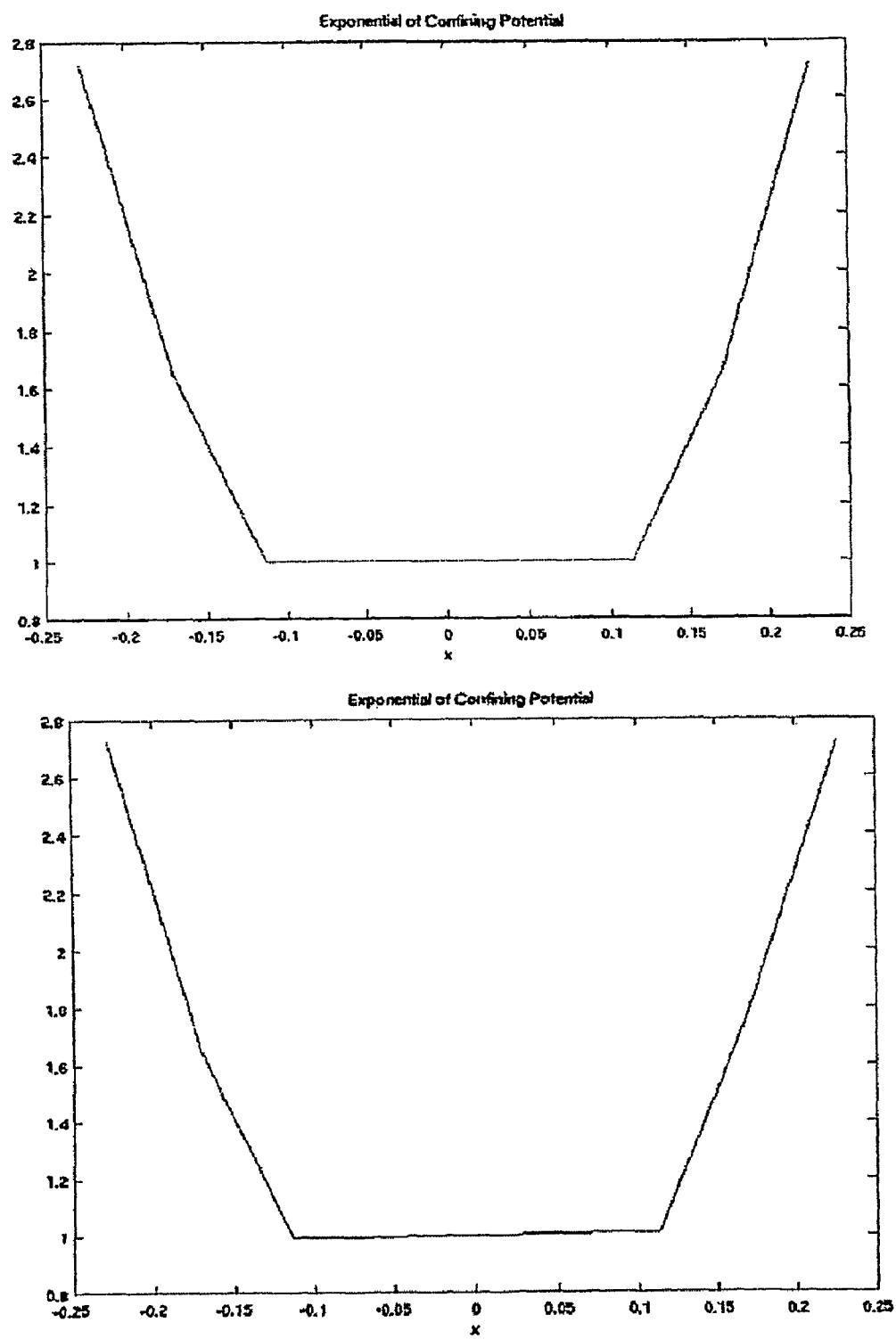
FIG. 15 shows the initial value (above) and computed optimal potential (below) for the functional $J_\alpha$ with $\alpha=200$.
Figure 17:
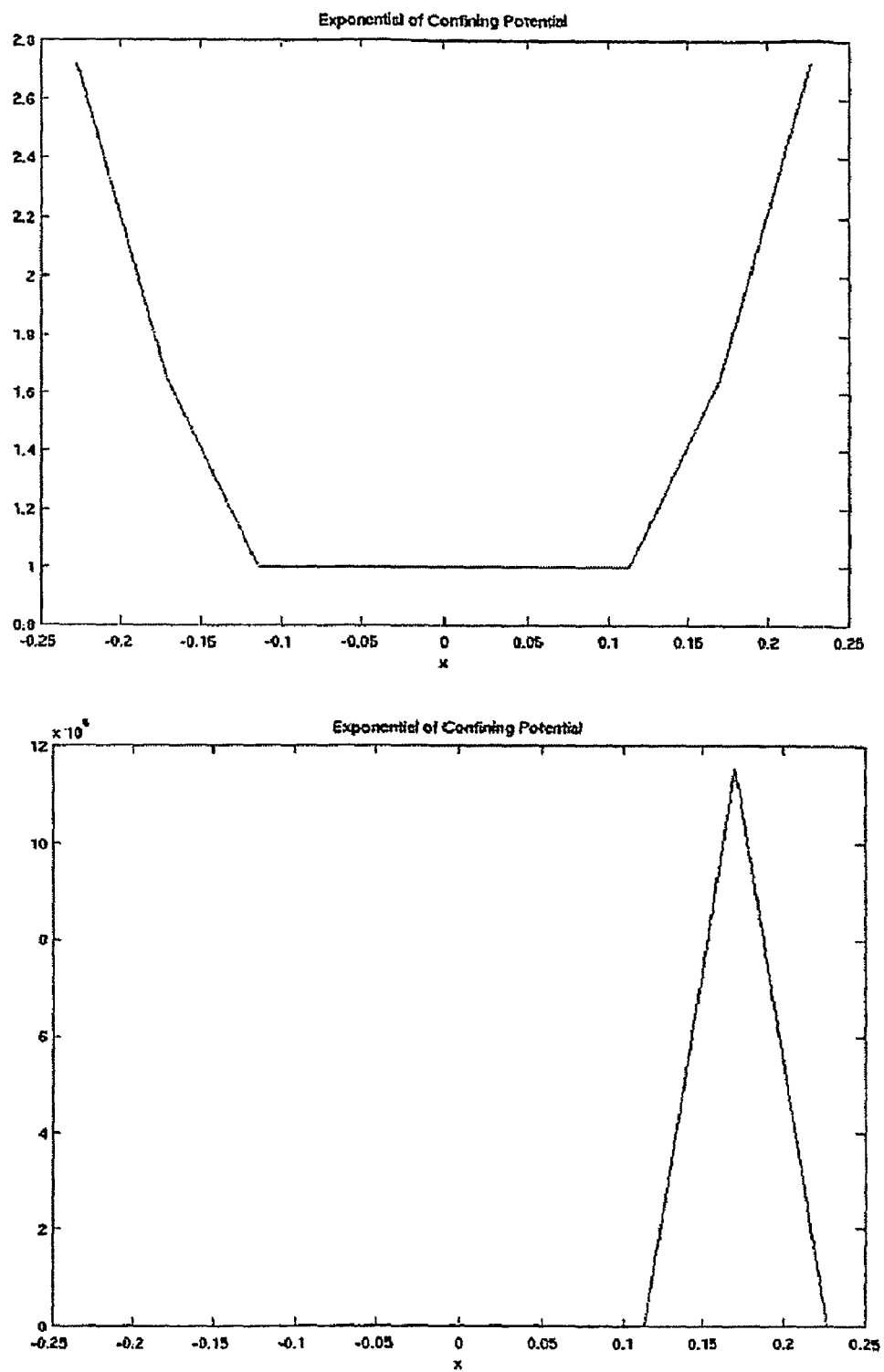
FIG. 17 shows the initial value (above) and computed optimal potential (below) for the functional J.

A special design case (with parameter $\alpha=200$) is illustrated in the plot in FIG. 15, which shows the evolution of the objective functional (black) as well as its first part, the negative permeability ratio $-S_{Na}(P)/S_{Ca}(P)$ during the iteration until convergence. One observes that an increase in the selectivity measure of more than 100% is achieved by the optimization. The initial value used for the optimization and the final result are plotted in FIG. 17. One observes that the two potentials are still very close, so the structure has not been changed completely implying that the modification could be built without too much trouble using techniques of the field of site-selected mutagenesis.

Figure 14:
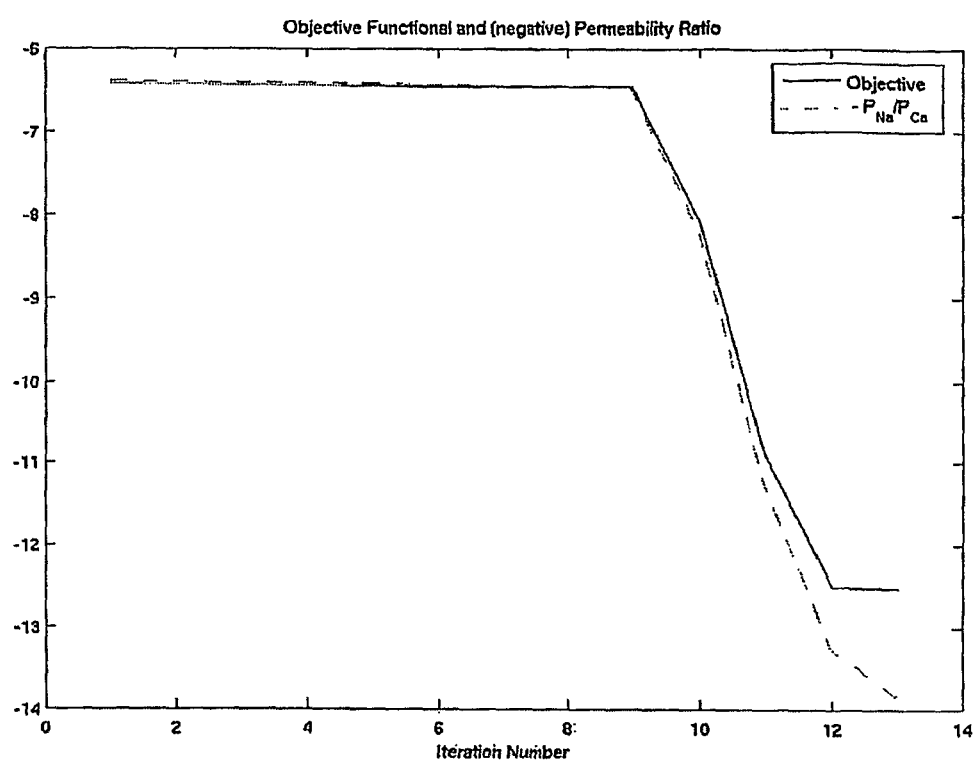
FIG. 14 shows the objective functional $J_\alpha(P_n)$ for $\alpha=200$ and negative permeability ratio as a function of the iteration number.
Figure 16:
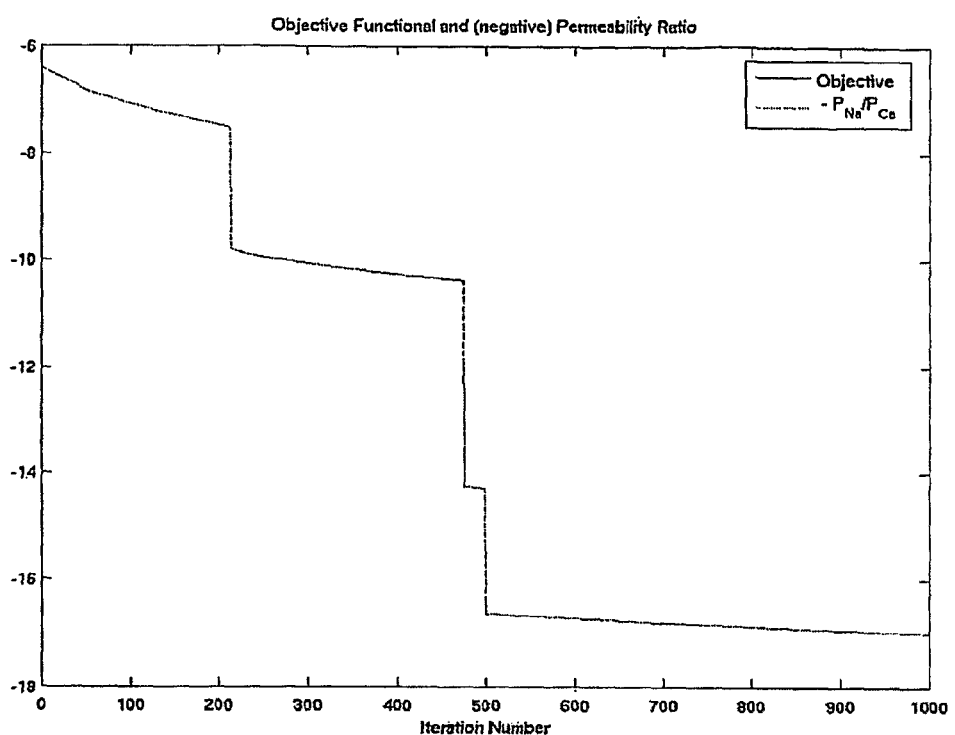
FIG. 16 shows the objective functional $J(P_n)$ equal to the negative permeability ratio as a function of the iteration number.

For comparison (and illustration of instabilities), also the classical approach of just minimizing the negative permeability ratio is illustrated, with the same initial value and parameter settings, but with the objective functional $J(P):=-S_{Na}(P)/S_{Ca}(P)$. Again, FIG. 16 displays the objective functional during the iterations, the optimal solution is plotted in FIG. 17. One observes that in this case the gradient method needs many more iterations than with penalization, but even then does not yield a dramatic increase of permeability (around 17 instead of 14 for the penalized case). However, just one look at the optimal potential in the unpenalized case (FIG. 14) shows that the (small) increase in the ratio is caused by a blow-up in the potential (notice the vertical scale of $10^6$). Obviously, such extremely high potentials and forces will not be easy to realize in actual structures and so the resulting channel design will not be useful in practice, which is another point in favor of our regularization approach.

The regularization parameter $\alpha$ controls the balance between selectivity and departure from the initial design. If $\alpha$ is very large, then the minimizer of $J_\alpha$ will remain close to the initial guess. By solving the optimal design problem for smaller values of $\alpha$, one could achieve a further increase in the permeability ratio, but also the optimal potential (i.e., the solution of the optimal design problem) will take higher values and become more and more difficult to be realized. As $\alpha \to 0$, one observes similar unphysical solutions as the one shown in FIG. 14. So, regularization gives (in addition to the advantages discussed) even more flexibility in finding a compromise between different design goals.

We summarize by stating that our examples show that both the identification and the design goals can be achieved in a stable and efficient way by our approach based on regularization, as illustrated by the special case of using Tikhonov regularization with an iterative minimization of the Tikhonov functional (13), and that such results are not possible by standard approaches due the ill-posed nature of the inverse problems considered.

From the foregoing it will be observed that numerous modifications and variations can be effectuated without departing from the true spirit and scope of the novel concepts of the present invention. It is to be understood that no limitation with respect to the specific embodiment illustrated is intended or should be inferred. Each of the patents and articles cited herein is incorporated by reference. The use of the article "a" or "an" is intended to include one or more. The disclosure is intended to cover by the appended claims all such modifications as fall within the scope of the claims.

[1] R. G. Airapetyan, A. G. Ramm, A. B. Smirnova, Continuous methods for solving nonlinear ill-posed problems, Fields Institute Communications 25, 111-137 (2000)

[2] A. B. Bakushinskii, The problem of the convergence of the iteratively regularized Gauss-Newton method, Comput. Math. Math. Phys. 32, 1353-1359 (1992)

[3] H. Banks, K. Kunisch, Parameter Estimation Techniques for Distributed Systems, Birkhäuser, Boston (1989)

[4] A. Binder, H. W. Engl, C. W. Groetsch, A. Neubauer and O. Scherzer, Weakly closed nonlinear operators and parameter identification in parabolic equations by Tikhonov regularization, Appl. Anal. 55, 215-234 (1994) 637-659 (1973)

[5] D. Blaschke, A. Neubauer, O. Scherzer, On convergence rates for the iteratively regularized Gauss-Newton method, IMA Journal of Numerical Analysis 17, 421-436 (1997)

[6] M. Burger, Iterative regularization of a parameter identification problem occurring in polymer crystallization, SIAM J. Numer. Anal. 39 (2001), 1029-1055.

[7] M. Burger, A level set method for inverse problems, Inverse Problems 17, 1327-1356 (2001)

[8] M. Burger, A framework for the construction of level set methods for shape optimization and reconstruction, Interfaces and Free Boundaries 5, 301-329 (2003)

[9] M. Burger, S. Osher, Convergence rates of convex variational regularization, Inverse Problems 20 (2004), 1411-1421.

[10] M. Burger, H. W. Engl, A. Leitao, P. Markowich, On inverse problems for semiconductor equations, Milan J. Math. 72 (2004), 273-314.

[11] M. Burger, H. W. Engl, P. A. Markowich, P. Pietra, Identification of doping profiles in semiconductor devices, Inverse Problems 17, 1765-1795 (2001)

[12] M. Burger and W. Mühlhuber, Numerical approximation of an SQP-type method for parameter identification, SIAM J. Numer. Anal. 40 (2002), 1775-1797.

[13] M. Burger, R. Pinnau, Fast optimal design of semiconductor devices, SIAM J. Appl. Math. 64 (2003), 108-126.

[14] M. Burger, O. Scherzer, Regularization methods for blind deconvolution and blind source separation problems, Mathematics of Control, Signals and Systems 14 (2001), 358-383.

[15] C. Carthel, H. W. Engl, Identification of heat transfer functions in continuous casting of steel by regularization, J. Inv. Ill-Posed Problems 8, 677-693 (2000)

[16] D. Colton, R. Ewing, and W. Rundell, Inverse Problems in Partial Differential Equations, SIAM, Philadelphia (1990)

[17] D. Colton, R. Kress, Inverse Acoustic and Electromagnetic Scattering Theory, Springer, Berlin (1992)

[18] P. Deuflhard, H. W. Engl, O. Scherzer, A convergence analysis of iterative methods for the solution of nonlinear ill-posed problems under affinely invariant conditions, Inverse Problems 14, 1081-1106 (1998)

[19] P. P. B. Eggermont, Maximum entropy regularization for Fredholm integral equations of the first kind, SIAM J. Math. Anal. 24, 1557-1576 (1993)

[20] H. W. Engl, Regularization methods for the stable solution of inverse problems, Surveys on Mathematics for Industry 371-143 (1993)

[21] H. W. Engl, W. Grever, Using the L-curve for determining optimal regularization parameters, Numerische Mathematik 69, 25-31 (1994)

[22] H. W. Engl, C. W. Groetsch, Inverse and Ill-Posed Problems, Academic Press, Orlando, (1987)

[23] H. W. Engl, M. Hanke, A. Neubauer, Regularization of Inverse Problems, Kluwer Academic Publishers, Dordrecht (1996) (Paperback edition 2000)

[24] H. W. Engl, K. Kunisch and A. Neubauer, Convergence rates for Tikhonov regularization of nonlinear ill-posed problems, Inverse Problems 5, 523-540 (1989)

[25] H. W. Engl, G. Landl, Convergence rates for maximum entropy regularization, SIAM J. Numer. Anal. 30, 1509-1536 (1993)

[26] H. W. Engl, G. Landl, Maximum entropy regularization of nonlinear ill-posed problems, in: V. Lakshmikantham, ed., Proceedings of the First World Congress of Nonlinear Analysts, Vol. I, de Gruyter, Berlin, 513-525 (1996)

[27] H. W. Engl, A. K. Louis and W. Rundell (eds.), Inverse Problems in Geophysics, SIAM, Philadelphia, (1996)

[28] H. W. Engl, A. K. Louis, W. Rundell (eds.), Inverse Problems in Medical Imaging and Non-Destructive Testing, Springer, Vienna, N.Y. (1996)

[29] H. W. Engl, A. Neubauer, Convergence rates for Tikhonov regularization in finite dimensional subspaces of Hilbert scales, Proc. Amer. Math. Soc. 102, 587-592 (1988)

[30] H. W. Engl, W. Rundell (eds.), Inverse Problems in Diffusion Processes, SIAM, Philadelphia (1995)

[31] H. W. Engl, O. Scherzer, Convergence rate results for iterative methods for solving nonlinear ill-posed problems, in: D. Colton, H. W. Engl, A. K. Louis, J. McLaughlin, W. F. Rundell (eds.), Surveys on Solution Methods for Inverse Problems, Springer, Vienna/N.Y., 7-34 (2000)

[32] H. W. Engl, A. Wakolbinger, Continuity properties of the extension of a locally Lipschitz continuous map to the space of probability measures, Monatshefte f. Math. 100, 85-103 (1985)

[33] D. Gillespie, R. Eisenberg (2002), Physical descriptions of experimental selectivity measurements in ion channels, European Biophysics Journal 31 (2002), 454-466.

[34] D. Gillespie, W. Nonner, R. Eisenberg, Coupling Poisson-Nernst-Planck and density functional theory to calculate ion flux, J. Phys.: Condens. Matter 14 (2002), 12129-12145.

[35] D. Gillespie, W. Nonner, R. Eisenberg, Density functional theory of charged, hard-sphere fluids, Phys. Rev. E 68 (2003), 031503. with

[36] C. W. Groetsch, A note on segmenting Mann iterates, J. Math. Anal. Appl. 40, 369-372 (1972)

[37] C. W. Groetsch, Inverse Problems in the Mathematical Sciences, Vieweg, Braunschweig (1993)

[38] M. Hanke, A regularizing Levenberg-Marquardt scheme with applications to inverse groundwater filtration problems, Inverse Problems 13, 79-95 (1997)

[39] M. Hanke, A. Neubauer, O. Scherzer, A convergence analysis of the Landweber iteration for nonlinear ill-posed problems, Numerische Mathematik 72, 21-37 (1995)

[40] P. C. Hansen, D. P. O'Leary, The use of the L-curve in the regularization of discrete ill-posed problems, SIAM J. Sci. Comput. 14, 1487-1503 (1993)

[41] J. Haslinger, P. Neittaanmäki, Finite Element Approximation for Optimal Shape Design: Theory and Applications, John Wiley & Sons Ltd., Chichester (1988).

[42] M. Hinze, R. Pinnau, Optimal control of the drift-diffusion model for semiconductor devices, in: K. H. Hoffmann, et. al., eds. *Optimal Control of Complex Structures* (Birkhäuser, Basel, Berlin, 2002), 95-106.

[43] M. Hinze, R. Pinnau, An optimal control approach to semiconductor design, Math. Mod. Meth. Appl. Sci. (2002), 89-107

[44] B. Hoffmann, Mathematik inverser Probleme, Teubner, Stuttgart (1999)

[45] D. Isaacson, J. C. Newell, Electrical Impedance Tomography, SIAM Review 41, 85-101 (1999)

[46] V. Isakov, Inverse Problems in Partial Differential Equations, Springer, Berlin, N.Y. (1998)

[47] B. Kaltenbacher, On Broyden's method for nonlinear ill-posed problems, Numer. Funct. Anal. Opt. 19 (1998), 807-833

[48] B. Kaltenbacher, A. Neubauer, A. G. Ramm, Convergence rates of the continuous regularized Gauss-Newton method, J. Inv. Ill-Posed Problems 10, 261-280 (2002)

[49] B. Kaltenbacher, A. Neubauer, O. Scherzer, Iterative Regularization Methods for Nonlinear Ill-Posed Problems Springer, Dordrecht, 2006, to appear.

[50] A. Kirsch, An Introduction to the Mathematical Theory of Inverse Problems, Springer, New York (1996)

[51] G. Landl, R. S. Anderssen, Non-negative differentially constrained entropy-like regularization, Inverse Problems 12, 35-53 (1996)

[52] A. Leitao, O. Scherzer, On the relation between constraint regularization, level sets and shape optimization, Inverse Problems 19, L1-L11(2003) solutions, Inverse Problems 14, 1539-1550 (1998) in [22], 177-183

[53] A. K. Louis, Inverse und schlecht gestellte Probleme, Teubner, Stuttgart (1989) L.

[54] M. Z. Nashed, O. Scherzer, Least squares and bounded variation regularization with non-differentiable functional, Num. Funct. Anal. and Optimiz. 19, 873-901 (1998)

[55] M. Z. Nashed, O. Scherzer, Interactions of Inverse Problems and Imaging, Contemporary Mathematics, Vol. 313, AMS (2002) 28, 329-341 (1977)

[56] F. Natterer, The Mathematics of Computerized Tomography, Teubner, Stuttgart (I 986)

[57] A. Neubauer, Tikhonov regularization for non-linear ill-posed problems: optimal convergence rates and finite-dimensional approximation, Inverse Problems 5, 541-557 (1989)

[58] A. Neubauer, O. Scherzer, Finite-dimensional approximation of Tikhonov regularized solutions of non-linear ill-posed problems, Numer. Funct. Anal. and Optimiz. 11, 85-99 (1990)

[59] W. Nonner, L. Catacuzzeno, R. Eisenberg, Binding and selectivity in L-type Ca channels: a mean spherical approximation. Biophysical Journal 79 (2000), 1976-1992.

[60] S. Osher, M. Burger, D. Goldfarb, J. Xu, W. Yin, An iterative regularization method for total variation based image restoration, Multiscale Modelling and Simulation 4 (2005), 460-489.

[61] S. Osher, R. P. Fedkiw, Level Set Methods and Dynamic Implicit Surfaces, Springer, New York (2002)

[62] S. Osher, F. Santosa, Level set methods for optimization problems involving geometry and constraints I. Frequencies of a two-density inhomogeneous drum, J. Comp. Phys. 171, 272-288 (2001)

[63] R. Plato, G. Vainikko, On the regularization of projection methods for solving ill-posed problems, Numer. Math. 57, 63-79 (1990)

[64] E. Radmoser, O. Scherzer, J. Weickert, Scale-space properties of nonstationary iterative regularization methods, Journal of Visual Communication and Image Representation 11, 96-114 (2000)

[65] A. G. Ramm, Scattering by Obstacles, Reidel, Dordrecht, (1986)

[66] E. Resmerita, Regularization of ill-posed problems in Banach spaces: convergence rates, Inverse problems 21 (2005) 1303-1314.

[67] L. I. Rudin, S. Osher, Total variation based restoration with free local constraints, Proc. of IEEE Int. Conf. on Inage Processing, Austin, Tx., 31-35 (1994)

[68] F. Santosa, A level-set approach for inverse problems involving obstacles, ESAIM: Control, Optimization and Calculus of Variations 1, 17-33 (1996) problems, Numerische Mathematik 80, 579-600 (1998)

[69] O. Scherzer, Explicit versus implicit relative error regularization on the space of functions of bounded variation, Contemporary Methematics 313, 171-198 (2002)

[70] O. Scherzer, Scale space methods for denoising and inverse problems, Advances in Imaging and Electron Physics 128, 445-530 (2003).

[71] O. Scherzer, H. W. Engl, K. Kunisch, Optimal a-posteriori parameter choice for Tikhonov regularization for solving nonlinear ill-posed problems, SIAM J. Numer. Anal. 30, 1796-1838 (1993)

[72] O. Scherzer, C. W. Groetsch, Scale-Space and Morphology in Computer Vision, Springer Lecture Notes in Computer Science 2106, Springer, Berlin, 317-325 (2001)

[73] J. A. Sethian, Level Set Methods and Fast Marching Methods, Cambridge University Press, 2nd edition, Cambridge (1999)

[74] U. Tautenhahn, On the asymptotic regularization of nonlinear ill-posed problems, Inverse Problems 10, 1405-1418 (1994) Sciences, VSP, Utrecht, 1992, 214-223, (1992)

[75] C. R. Vogel, Non-convergence of the L-curve regularization parameter selection method, Inverse Problems 12, 535-547 (1996)

[76] G. Wahba, Spline Models for Observational Data, SIAM, Philadelphia (1990)

[77] Selberherr, S. Analysis and Simulation of Semiconductor Devices (Springer-Verlag, New York, 1984)

[78] Jerome, J. W. Mathematical Theory and Approximation of Semiconductor Models (Springer-Verlag, New York, 1995)

[79] Bank, R. E., Rose, D. J. & Fichtner, W. Numerical Methods for Semiconductor Device Simulation. IEEE Trans. on Electron Devices ED-30, 1031-1041 (1983)

[80] Gummel, H. K. A self-consistent iterative scheme for one-dimensional steady-state transistor calculations. IEEE Trans. Electron Devices ED-11, 445-465 (1964)

[81] Scharfetter, D. L. & Gummel, H. K. Large signal analysis of a silicon read diode oscillator. IEEE Trans Electron Devices, 64-77 (1969)

[82] Kerkhoven, T. On the effectiveness of Gummel's method. SIAM J. Sci. & Stat. Comp. 9, 48-60 (1988)

[83] Kerkhoven, T. & Saad, Y. On acceleration methods for coupled nonlinear elliptic systems. Numer. Math 57, 525-548 (1992)

[84] Kerkhoven, T. & Jerome, J. W. L(infinity) stability of finite element approximations to elliptic gradient equations. Numer. Math. 57, 561-575 (1990)

[85] Hess, K., Leburton, J. P. & Ravaioli, U. Computational Electronics: Semiconductor Transport and Device Simulation (Kluwer, Boston, Mass. USA, 1991)

[86] Hess, K. Monte Carlo Device Simulation: Full Band and Beyond (Kluwer, Boston, Mass. USA, 1991)

[87] Damocles. in http://www.research.ibm.con/DAMOCLES/home.html (2005)

[88] Bank, R. E., Burgler, J., Coughran, W. M., Jr., W. Fichtner & Smith, R. K. Recent Progress in Algorithms for Semiconductor Device Simulation. International Series of Numerical Mathematics 93, 125-140 (1990)

[89] Jacoboni, C. & Lugli, P. The Monte Carlo Method for Semiconductor Device Simulation (Springer Verlag, New York, 1989)

[90] Grasser, T., Tang, T., Kosina, H., Selberherr, S. A review of hydrodynamic and energy-transport models for semiconductor device simulation. Proceedings of the IEEE 91 (2003)

[91] Ferry, D. K. Semiconductor Transport (Taylor and Francis, N.Y., 2000)

[92] Hille, B., *Ionic Channels of Excitable Membranes*. 3rd ed. 2001, Sunderland: Sinauer Associates Inc. 1-814.

[93] Attwell, D. in Membrane Transport Processes Vol 3 (eds. Stevens, C. F. & Tsien, R. W.) (Raven Press, New York, 1979).

[94] Attwell, D. & Jack, J. J. B. The Interpretation of Membrane Current voltage relations: a Nernst Planck Analysis. Prog. Biophysics and Molecular Biology 34, 81-107 (1978).

[95] Zachariae, U., Koumanov, A., H. Engelhardt, and Karshikoff, A. 2002. Electrostatic properties of the anion selective porin Omp32 from *Delftia acidovorans* and of the arginine cluster of bacterial porins. *Prot. Sci.*, 11, 1309-1319.

[96] Tsushima, R. G., Li, R. A., Backx, P. H. 1997. Altered ionic selectivity of the sodium channel revealed by cysteine mutations within the pore. *J. Gen. Physiol.*, 109, 463-475.

[97] Lou, K-L., Saint, N., Prilipov, A., Rummel, G., Benson, S. A., Rosenbusch, J. P., and Schirmer, T. 1996. Structural and functional characterization of OmpF porin mutants selected for larger pore size. *J. Biol. Chem.*, 271, 20669-20675.

[98] Lougheed, T., Zhang, Z., Woolley, G. A., Borisenko, V. 2004. Engineering charge selectivity in model ion channels. *Bioorganic & Medical Chemistry.*, 12, 1337-1342.

[99] Miedema, H., Meter-Arkema, A., Wierenga, J., Tang, J., Eisenberg, B., Nonner, W., Hektor, H., Gillespie, D., and Meijberg, W. 2004. Permeation properties of an engineered bacterial OmpF porin containing the EEEE-locus of $Ca^{2+}$ channels. *Biophys. J.*, 87, 3137-3147.

[100] Nestorovich, E. M., Rostovtseva, T. K., Bezrukov, M. 2003. Residue ionization and ion transport through OmpF channels. *Biophys. J.*, 85, 3718-3729.

[101] Noskov, S. Y., Bemèche, S., and Roux, B. 2004. Control of ion selectivity in potassium channels by electrostatic and dynamic properties of carbonyl ligands. *Nature,* 431, 830-834.

[102] Pérez-Garćia, M. T., Chiamvimonvat, N., Marban, E., and Tomaselli, G. F. 1996. Structure of the sodium channel pore revealed by serial cysteine mutagenesis. *Proc. Natl. Acad. Sci. USA.*, 93, 300-304.

[103] Phale, P. S., A. Philippsen, C. Widmer, V. P. Pahe, J. P. Rosenbusch, and T. Schirmer.

2001. Role of charged residues at the OmpF porin channel constriction probed by mutagenesis and simulation. *Biochemistry.* 40:6319-6325.

[104] Saint, N., K-L. Lou, C. Widmer, M. Luckey, T. Schirmer, and J. P. Rosenbusch. 1996. Structural and functional characterization of OmpF porin mutants selected for larger pore size. *J. Biol. Chem.*, 271, 20676-20680.

[105] Sakai, N., Sordé, N. Das, G., Perrottet, P., Gerard, D., Matile, S. 2003. Synthetic multifunctional pores: deletion and inversion of anion/cation selectivity using pM and pH. *Org. Biomol. Chem.*, 1, 1226-1231.

[106] Saxena, K., V. Drosou, E. Maier, R. Benz, and B. Ludwig. 1999. Ion selectivity reversal and induction of voltage-gating by site-directed mutations in the *Paracoccus denitrificans* porin. *Biochemistry.* 38:2206-2212.

[107] Kienker, P. K., and Lear, J. D. 1995. Charge selectivity of the designed uncharged peptide ion channel Ac-$(LSSLLSL)_3$-$CONH_2$. *Biophys. J.*, 68, 1347-1358.

[108] Koch, S. E., Bodi, I., Schwartz, A., and Varadi, G. 2000. Architecture of $Ca^{2+}$ channel pore-lining segments revealed by covalent modification of substituted cysteines. *J. Biol. Chem.*, 275, 34493-34500.

[109] Jeon, Y. J., et al., 2004. Artificial ion channel formed by cucurbit[n]uril derivatives with a carbonyl group fringed portal reminiscent of the selectivity filter of $K^+$ channels. *J. A. Chem. Soc.*, 126, 15944-15945.

[110] Danelon, C., A. Suenaga, M. Winterhalter, and I. Yamato. 2003. Molecular origin of the cation selectivity in OmpF porin: single channel conductances vs. free energy calculation. *Biophys. Chem.*, 104, 591-603.

[111] Gocke, I., Bainbridge, G., Lakey, J. H. 1997. Stabilising and destabilising modifications of cysteines in the *E. coli* outer membrane porin protein OmpC. *FEBS Let.*, 411, 201-205.

[112] Gu, L-Q., Serra, M. D., Vincent, J. B., Vigh, G., Cheley, S., Braha, O., Bayley, H. 2000. Reversal of charge selectivity in transmembrane protein pores by using noncovalent molecular adapters. *Proc. Nat. Acad. Sci. USA.*, 97, 3959-3964.

[113] Brunen, M., and H. Engelhardt. 1995. Significance of positively charged amino acids for the function of the *Acidovorax delafieldii* porin Omp34. *FEMS Microbiology Letters.* 126:127-132.

[114] Carrillo-Trip, M., Saint-Martin, H., Ortega-Blake, 1. 2004. Minimalist molecular model for nanopore selectivity. *Phys. Rev. Letters.* 93(16).

[115] Chiamvimonvat, N., Pérez-Garćia, M. T., Tomaselli, G. F., Marban, E. 1996. Control of ion flux and selectivity by negatively charged residues in the outer mouth of rat sodium channels. *J. Physiol.* 491, 51-59.

[116] Bayley, H., and Jayasinghe, L. 2004. Functional engineered channels and pores. *Mol. Membrane Biol.*, 21, 209-220.

[117] Borisenko, V., Samsom, M. S. P., Woolley, G. A. 2000. Protonation of lysine residues inverts cation/anion selectivity in a model channel. *Biophys. J.*, 78, 1335-1348.

[118] Bredin, J., Saint, N., Malléa, M., Dé, E., Molle, G., Pagès, J-M., and Simonet, V. 2002. Alteration of pore properties of *Escherichia coli* OmpF induced by mutation of key residues in anti-loop 3 region. *Biochem. J.*, 363, 521-528.

[118] Favre, I., E. Moczydlowski, and L. Schild. 1996. On the structural basis for ionic selectivity among $Na^+$, $K^+$, and $Ca^{2+}$ in the voltage-gated sodium channel. *Biophys. J.* 71:3110-3125.

[120] Heinemann, S. H., H. Terlau, W. Stühmer, K. Imoto, and S, Numa. 1992. Calcium channel characteristics conferred on the sodium channel by single mutations. *Nature.* 356:441-443.

[121] Im, W., and B. Roux. 2002 a. Ion permeation and selectivity of OmpF porin: a theoretical study based on molecular dynamics, Brownian dynamics, and continuum electrodiffusion theory. *J. Mol. Biol.* 322:851-869.

[122] Danelon, C., A. Suenaga, M. Winterhalter, and I. Yamato. 2003. Molecular origin of the cation selectivity in OmpF porin: single channel conductances vs. free energy calculation. *Biophys. Chem.* 104:591-603.

[123] McCleskey, E. W. 2000. Ion channel selectivity using an electric stew. *Biophys. J.* 79:1691-1692.

[124] Nestorovich, E. M., T. K. Rostovtseva, and S. M. Bezrukov. 2003. Residue ionization and ion transport through OmpF channels. *Biophys. J.* 85:3718-3729.

[125] Sun, Y-M., I. Favre, L. Schild, and E. Moczydlowski. 1997. On the structural basis for size-selective permeation of organic cations through the voltage-gated sodium channel. *J. Gen Physiol.* 110:693-715.

[126] Yamaoka, K., E. Kinoshita, and 1. Seyama. 2003. Altering ion selectivity of the L-type $Ca^{2+}$ channel cloned from frog cardiac myocytes. *Biophys. J. Supplement,* 84, poster #1959.

[127] Yang, J., P. T. Ellinor, W. A. Sather, J. I. F. Zhang, and R. W. Tsien. 1993. Molecular determinants of $Ca^{2+}$ selectivity and ion permeation in L-type $Ca^{2+}$ channels. *Nature.* 366: 158-161.

[128] Yue, L., B. Navarro, D. Ren, A. Ramos, and D. E. Clapham. 2002. The cation selectivity filter of the bacterial sodium channel, NaChBac. *J. Gen. Physiol.* 120:845-853.

[129] Brezzi, F., Fortin, M., 1991. *Mixed and Hybrid Finite Element Methods*. Springer-Verlag, New York.

[130] Ion Channels: Methods And Protocols (Methods in Molecular Biology) James D. Stockand (Editor), Mark S. Shapiro (Editor), Humana Press 2006 (can be ordered from Amazon.com or Humana Press for scheduled July 2006 release).

APPENDIX

Model Equations for LCC Example

Involved species and related unknowns (see also Table 1):
1. $Ca^{2+}$: Density $\rho_1$, flux $J_1$, electrochemical potential $\mu_1$
2. $Na^+$: Density $\rho_2$, flux $J_2$, electrochemical potential $\mu_2$
3. $Cl^{-1}$: Density $\rho_3$, flux $J_3$, electrochemical potential $\mu_3$
4. $H_2O$: Density $\rho_4$, flux $J_4$, electrochemical potential $\mu_4$
5. $O^{-1/2}$: Density $\rho_5$, flux $J_5$, electrochemical potential $\mu_5$
6. Electrostatic potential $\phi$ Equations to be solved for $x \in (-L, L)$ Poisson Equation $$-\frac{1}{A(x)}\frac{d}{dx}\left(\varepsilon A(x)\frac{d\phi}{dx}\right) = e\sum_i z_i \rho_i(x) \tag{1}$$

Constitutive Laws (i=1, 2, 3, 4, 5):

$$-J_i = \frac{1}{kT} D_i(x) A(x) \rho_i(x) \frac{d\mu_i}{dx} \tag{2}$$

Continuity Equations (i=1, 2, 3, 4, 5)

$$\frac{dJ_i}{dx} = 0 \tag{3}$$

Electrochemical Potentials (i=1, 2, 3, 4, 5)

$$\mu_i(x) = \mu_i^0(x) + \mu_i^{id}(x) + \mu_i^{ex}(x) \tag{4}$$

Constraining Potential $\mu_i^0(x)$ (i=1, 2, 3, 4)

$$\mu_i^0(x) = 0 \tag{5}$$

Constraining potential $\mu_5^0(x)$ to be determined as solution of the inverse problem, therefore used with varying values during the outer iteration for the solution of the inverse problem Ideal Components $\mu_i^{id}(x)$ (i=1, 2, 3, 4, 5)

$$\mu_i^{id}(x) = z_i e\phi(x) + kT\ln\left(\frac{\rho_i(x)}{\rho_{scale}}\right) \tag{6}$$

Excess Components $\mu_i^{ex}(x)$ (i=1, 2, 3, 4, 5)

$$\mu_i^{ex} = \mu_i^{HS} + \mu_i^{ES} \tag{7}$$

Hard-Sphere Components $\mu_i^{HS}(x)$ (i=1, 2, 3, 4, 5)

$$\mu_i^{HS}(x) = kT\sum_\alpha \int_{x-R_i}^{x+R_i} \frac{\partial \Phi_{HS}}{\partial n_\alpha}(x') W_i^{(\alpha)}(x-x') dx' \tag{8}$$

"Antisymmetrized" Excess Free Energy Density $$\Phi_{HS}(\{n_\alpha(x)\}) = \tag{9}$$
$$-n_0\ln(1-n_3) + \frac{n_1 n_2 - n_{v1} n_{v2}}{1-n_3} + \frac{n_2^3}{24\pi(1-n_3)^2}\left(1 - \frac{n_{v2} n_{v2}}{n_2^2}\right)^3$$

Density Averages ($\alpha$0, 1, 2, 3, V1, V2)

$$n_\alpha(x) = \sum_i \int_{x-R_i}^{x+R_i} \rho_i(x') W_i^{(\alpha)}(x'-x) dx' \tag{10}$$

Weights (i=1, 2, 3, 4, 5)

$$W_i^{(2)}(r) = 2\pi R_i \tag{11}$$

$$W_i^{(3)}(r) = \pi(R_i^2 - r^2) \tag{12}$$

$$W_i^{(v2)}(r) = 2\pi r(1,0,0) \tag{13}$$

$$4\pi R_i^2 W_i^{(0)}(r) = 4\pi R_i W_i^{(1)}(r) = W_i^{(2)}(r) \tag{14}$$

$$4\pi R_i W_i^{(v1)}(r) = W_i^{(v2)}(r). \tag{15}$$

Electrostatic Components $\mu_i^{ES}(x)$ (i=1, 2, 3, 4, 5)

$$\mu_i^{ES}(x) = \tag{16}$$
$$\mu_i^{ES}(\{\rho_k^{ref}(x)\}) - \sum_j \frac{z_i z_j e^2}{8\varepsilon\varepsilon_0} \frac{1}{\lambda_i \lambda_j} \times \int_{x-R_{ij}}^{x+R_{ij}} \Delta\rho_i(x')\left(\frac{1}{3}R_{ij}^3 + \lambda_{ij}^2 R_{ij} - \lambda_{ij} R_{ij}^2 + \lambda_{ij}(x'-x)^2 - \frac{1}{3}|x'-x|^3 - \lambda_{ij}^2|x'-x|\right)dx'$$

Density Expansion $$\Delta\rho_i(x) = \rho_i(x) - \rho_i^{ref}(x) \tag{17}$$

Radii (i, j=1, 2, 3, 4, 5)

$$R_{ij} = R_i + R_j \tag{18}$$

Capacitance Lengths (i, j=1, 2, 3, 4, 5)

$$\lambda_{ij} = \lambda_i + \lambda_j \tag{19}$$

$$\lambda_k(x) = R_k + s(x) \tag{20}$$

Screening Length $$s(x) = \frac{1}{2\Gamma(x)} \tag{21}$$

MSA Screening Parameter $$4\Gamma(x)^2 = \frac{e^2}{kT\varepsilon\varepsilon_0}\sum_j \rho_j(x)\left[\frac{z_j - \eta(x)R_j}{1+\Gamma(x)R_j}\right]^2 \quad (22)$$

MSA Parameters $$\eta(x) = \frac{1}{\Omega(x)}\frac{\pi}{2\Delta(x)}\sum_j \frac{\rho_j(x)R_j z_j}{1+\Gamma(x)R_j} \quad (23)$$

$$\Omega(x) = 1 + \frac{\pi}{2\Delta(x)}\sum_j \frac{\rho_j(x)R_j^3}{1+\Gamma(x)R_j} \quad (24)$$

$$\Delta(x) = 1 - \frac{\pi}{6}\sum_j \frac{d\rho_j}{dx}(x)R_j^3 \quad (25)$$

Reference Fluid Component (k=1, 2, 3, 4, 5)

$$\rho_k^{ref}(x) = \int \overline{\rho}_k(x')\omega(x;x')dx' \quad (26)$$

Weight Function $$\omega(x;x') = \begin{cases} \dfrac{A(x')}{2R_{filter}(x)} & \text{if } |x-x'| \le R_{filter}(x) \\ 0 & \text{if } |x-x'| > R_{filter}(x) \end{cases} \quad (27)$$

Filter Radius $$R_{filter}(x) = \frac{\sum_k \overline{\rho}_k(x)R_k}{\sum_k \overline{\rho}_k(x)} + s(x). \quad (28)$$

Auxiliary Densities $$\overline{\rho}_k(x) = \alpha\rho_k^*(x) \; (z_k \ge 0) \quad (29)$$

$$\overline{\rho}_k(x) = \alpha B \rho_k^*(x) \; (z_k < 0) \quad (30)$$

Normalization Parameters $$\alpha = \frac{\sum_k z_k^2 \rho_k^*(x)}{\sum_{z_k \ge 0} z_k^2 \rho_k^*(x) + B\sum_{z_k<0} z_k^2 \rho_k^*(x)} \quad (31)$$

$$B = \frac{\sum_{z_k \ge 0} z_k \rho_k^*(x)}{\sum_{z_k<0} |z_k| \rho_k^*(x)}. \quad (32)$$

Initial densities $\rho_k^*$ determined through self-consistency iteration

Boundary conditions for x=±L

Values of $\rho_k(\pm L)$ (k=1, 2, 3, 4) specified, see Table 1. Left boundary values varying due to varying concentrations in the different setups. For $\rho_5$ we have Neumann boundary conditions $$\frac{d\rho_5}{dx}(-L) = \frac{d\rho_5}{dx}(L) = 0,$$

and the condition $$N_5 = \int_{-L}^{L} A(x)\rho_5(x)dx, \quad (33)$$

with $N_5=8$, except for the first example.

Values of $\phi(L)=0$, $\phi(-L)=U$, where U denotes the applied voltage, varying in the different setups.

Parameter Values

Dielectric coefficient $\in_0 = 8.85 \times 10^{-12}$ F/m

Relative dielectric coefficient $\in = 78$

Elementary charge $e = 1.602 \times 10^{-19}$ C

Boltzmann constant $k = 1.381 \times 10^{-23}$ joules/deg = $8.62 \times 10-5$ electron-volts/deg Temperature T=300 K.

The further parameters needed in the above equation are given in the following table (value of $D_5$ does not matter since the boundary conditions imply $d\mu_5/dx=0$):

| | k | | | | |
|---|---|---|---|---|---|
| | 1 | 2 | 3 | 4 | 5 |
| Species | $Ca^{2+}$ | $Na^+$ | $Cl^{-1}$ | $H_2O$ | $O^{-1/2}$ |
| $D_k$ (bath) (units in m²/s) | $7.9 \times 10^{-10}$ | $1.3 \times 10^{-9}$ | $2.03 \times 10^{-9}$ | $2.13 \times 10^{-9}$ | |
| $D_k$ (channel) (units in m²/s) | $7.9 \times 10^{-10}$ | $3.25 \times 10^{-12}$ | $3.25 \times 10^{-12}$ | $2.13 \times 10^{-11}$ | |
| $R_k$ (units in m) | $1 \times 10^{-10}$ | $1 \times 10^{-10}$ | $1.8 \times 10^{-10}$ | $1.4 \times 10^{-10}$ | $1.4 \times 10^{-10}$ |

The invention claimed is:

1. A method for determining a structure of permanent charge for an ion channel from information comprising:
   providing a computer having a memory, a processor having access to the memory;
   providing one or more computer programs comprising algorithms that:
   implement a regularizing family of equations that approximate a model of ion channel behavior that relates the function of the ion channel to at least the structure of permanent charge within the ion channel, the concentration of at least one ion species present in the region inside or adjacent to the ion channel, and boundary conditions to generate a regularized solution;

algorithms implementing an abstract operator so as to provide a closeness of the regularized solution to a solution provided by the abstract operator;

algorithms implementing stable and convergent algorithms that determine a stability for the regularized solution;

algorithms implementing a regularization parameter, the regularization parameter determining a balance between the stability of the regularized solution and the accuracy of the regularized solution; and algorithms to adjust the provided information in accordance with the regularizing family of equations until a regularized solution of balanced accuracy and stability is obtained;

providing the computer memory with the at least one computer program;

providing information including at least the concentration of the at least one ion species present in the region inside or adjacent to the ion channel and the boundary conditions;

providing the computer memory with the information;

providing the processor with the computer program and the information stored in the memory;

processing the information with the computer program to:
obtain a regularized solution;

estimate the closeness of the regularized solution to a solution provided by an abstract operator to obtain an accuracy of the regularized solution;

determining the stability of the regularized solution;

determining through computer code using the regularization parameter, the balance between the stability and accuracy of the regularized solution;

as necessary, adjust the provided information in accordance with the regularizing family of equations until a regularized solution of balanced accuracy and stability is obtained.

2. The method of claim 1, wherein the family of equations comprises:
a forward model of ion channel behavior; and
the information further comprises:
information regarding the structure of permanent charge for a control ion channel;
information for a plurality of sets of mobile species concentration information, a set of mobile species concentration information comprising a concentration of the first mobile species and a concentration of the second mobile species;
information for a corresponding ensemble of data for the relationship of current to voltage for the control ion channel for each of the plurality of sets of mobile species concentration information.

3. The method of claim 1, wherein:
the computer program for solving the forward model of ion channel behavior for the control ion channel further comprises;
providing a fast and accurate algorithm for the forward model, and
providing algorithms to determine an accuracy for the forward model;
and the processing further includes:
solving the forward model; and
determining an accuracy for the forward model.

4. The method of claim 3, wherein the ion channel model is a Poisson-Plank-Nernst model.

5. The method of claim 1, wherein regularizing uses regularization methods from the group consisting of variational and iterative approaches.

* * * * *